(12) United States Patent
Caffes et al.

(10) Patent No.: US 10,966,709 B2
(45) Date of Patent: *Apr. 6, 2021

(54) DEVICE FOR SUTURE ATTACHMENT FOR MINIMALLY INVASIVE HEART VALVE REPAIR

(71) Applicant: NeoChord, Inc., St. Louis Park, MN (US)

(72) Inventors: Levi Caffes, Denver, CO (US); Joel Helgerson, Erie, CO (US); Andrew Schifle, Superior, CO (US); Daryl Edmiston, Draper, UT (US); Graham Garvin, Redwood City, CA (US)

(73) Assignee: NeoChord, Inc., St. Louis Park, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/564,887

(22) Filed: Sep. 9, 2019

(65) Prior Publication Data

US 2020/0093478 A1 Mar. 26, 2020

Related U.S. Application Data

(60) Provisional application No. 62/728,349, filed on Sep. 7, 2018.

(51) Int. Cl.
*A61B 17/04* (2006.01)
*A61B 17/29* (2006.01)
*A61B 17/00* (2006.01)

(52) U.S. Cl.
CPC ...... *A61B 17/0469* (2013.01); *A61B 17/0485* (2013.01); *A61B 17/2909* (2013.01);
(Continued)

(58) Field of Classification Search
CPC ...... A61B 17/0482; A61B 2017/00243; A61B 17/0469; A61B 2017/2926; A61B 2017/2947
See application file for complete search history.

(56) References Cited

U.S. PATENT DOCUMENTS 2,751,908 A 6/1956 Wallace
3,664,330 A 5/1972 Deutsch
(Continued)

FOREIGN PATENT DOCUMENTS

EP 1039851 B1 7/2005
EP 1637091 A2 3/2006
(Continued)

OTHER PUBLICATIONS

PCT International Search Report and Written Opinion, PCT/US2019/050210, dated Dec. 2, 2019, 5 pages.
(Continued)

*Primary Examiner* — Shaun L David
*Assistant Examiner* — Christina C Lauer
(74) *Attorney, Agent, or Firm* — Patterson Thuente Pedersen, P.A.

(57) ABSTRACT

Disclosed herein are minimally invasive systems and methods for intravascularly accessing the heart and performing a transcatheter repair of a heart valve by inserting a suture as an artificial chordae into a heart valve leaflet. In various embodiments, such systems and methods can be employed in other heart valve repair procedures such an edge to edge repair to coapt leaflets by inserting one or more sutures that retain the leaflets in a coapted positioned or inserting a suture to repair a tear in a leaflet, for example.

20 Claims, 24 Drawing Sheets

(52) U.S. Cl.
CPC ............... *A61B 2017/0038* (2013.01); *A61B 2017/00243* (2013.01); *A61B 2017/00867* (2013.01); *A61B 2017/047* (2013.01); *A61B 2017/0496* (2013.01); *A61B 2017/2926* (2013.01)

(56) References Cited

U.S. PATENT DOCUMENTS

| | | | |
|---|---|---|---|
| 3,667,474 A | 6/1972 | Lapkin | |
| 3,842,840 A | 10/1974 | Schweizer | |
| 4,258,716 A | 3/1981 | Sutherland | |
| 4,351,345 A | 9/1982 | Carney | |
| 4,759,348 A | 7/1988 | Cawood | |
| 4,836,204 A | 6/1989 | Landymore et al. | |
| 4,935,027 A | 6/1990 | Yoon | |
| 4,957,498 A | 9/1990 | Caspari | |
| 4,967,498 A | 9/1990 | Caspari | |
| 4,960,424 A | 10/1990 | Grooters | |
| 4,967,798 A | 11/1990 | Hammer | |
| 4,972,874 A | 11/1990 | Jackson | |
| 5,053,013 A | 10/1991 | Ensminger | |
| 5,059,201 A | 10/1991 | Asnis | |
| 5,211,650 A | 5/1993 | Noda | |
| 5,297,536 A | 3/1994 | Wilk | |
| 5,304,185 A | 4/1994 | Taylor | |
| 5,312,423 A * | 5/1994 | Rosenbluth | A61B 17/12013 606/139 |
| 5,336,229 A | 8/1994 | Noda | |
| 5,383,877 A | 1/1995 | Clarke | |
| 5,431,666 A | 7/1995 | Sauer et al. | |
| 5,452,733 A | 9/1995 | Sterman | |
| 5,474,519 A | 12/1995 | Bloomer | |
| 5,547,455 A | 8/1996 | McKenna et al. | |
| 5,556,411 A | 9/1996 | Taoda et al. | |
| 5,571,215 A | 11/1996 | Sterman | |
| 5,601,578 A | 2/1997 | Murphy | |
| 5,626,607 A | 5/1997 | Malecki | |
| 5,653,716 A | 8/1997 | Malo et al. | |
| 5,665,100 A | 9/1997 | Yoon | |
| 5,667,472 A | 9/1997 | Finn et al. | |
| 5,667,473 A | 9/1997 | Finn et al. | |
| 5,667,478 A | 9/1997 | McFarlin et al. | |
| 5,693,091 A | 12/1997 | Larson, Jr. et al. | |
| 5,728,113 A | 3/1998 | Sherts | |
| 5,762,458 A | 6/1998 | Wang et al. | |
| 5,762,613 A | 6/1998 | Sutton et al. | |
| 5,766,163 A | 6/1998 | Mueller et al. | |
| 5,769,791 A | 6/1998 | Benaron et al. | |
| 5,772,597 A | 6/1998 | Goldberger et al. | |
| 5,772,672 A | 6/1998 | Toy et al. | |
| 5,785,658 A | 7/1998 | Benaron et al. | |
| 5,797,960 A | 8/1998 | Stevens et al. | |
| 5,830,231 A | 11/1998 | Geiges, Jr. | |
| 5,839,639 A | 11/1998 | Sauer et al. | |
| 5,857,961 A | 1/1999 | Vanden Hoek et al. | |
| 5,897,564 A | 4/1999 | Schulze et al. | |
| 5,908,428 A | 6/1999 | Scirica et al. | |
| 5,908,429 A | 6/1999 | Yoon | |
| 5,919,128 A | 7/1999 | Fitch | |
| 5,961,440 A | 10/1999 | Schweich, Jr. | |
| 5,972,004 A | 10/1999 | Williamson et al. | |
| 5,972,030 A | 10/1999 | Garrison et al. | |
| 5,984,939 A | 11/1999 | Yoon | |
| 5,993,466 A | 11/1999 | Yoon | |
| 5,993,467 A | 11/1999 | Yoon | |
| 6,022,360 A | 2/2000 | Reimels et al. | |
| 6,045,497 A | 4/2000 | Schweich, Jr. | |
| 6,050,936 A | 4/2000 | Schweich, Jr. | |
| 6,053,933 A | 4/2000 | Balazs et al. | |
| 6,059,715 A | 5/2000 | Schweich, Jr. | |
| 6,077,214 A | 6/2000 | Mortier et al. | |
| 6,117,144 A | 9/2000 | Nobles et al. | |
| 6,129,683 A | 10/2000 | Sutton et al. | |
| 6,149,660 A | 11/2000 | Laufer et al. | |
| 6,152,934 A | 11/2000 | Harper et al. | |
| 6,162,168 A | 12/2000 | Schweich, Jr. | |
| 6,162,233 A | 12/2000 | Williamson | |
| 6,165,119 A | 12/2000 | Schweich, Jr. | |
| 6,165,120 A | 12/2000 | Schweich, Jr. | |
| 6,165,183 A | 12/2000 | Kuehn et al. | |
| 6,178,346 B1 | 1/2001 | Amundson et al. | |
| 6,179,195 B1 | 1/2001 | Adams et al. | |
| 6,183,411 B1 | 2/2001 | Mortier et al. | |
| 6,190,357 B1 | 2/2001 | Ferrari et al. | |
| 6,234,079 B1 | 5/2001 | Chertkow | |
| 6,234,995 B1 | 5/2001 | Peacock, III | |
| 6,245,079 B1 | 6/2001 | Nobles et al. | |
| 6,260,552 B1 | 7/2001 | Mortier et al. | |
| 6,261,222 B1 | 7/2001 | Schweich, Jr. | |
| 6,264,602 B1 | 7/2001 | Mortier et al. | |
| 6,269,819 B1 | 8/2001 | Oz et al. | |
| 6,270,508 B1 | 8/2001 | KIleman et al. | |
| 6,283,993 B1 | 9/2001 | Cosgrove et al. | |
| 6,312,447 B1 | 11/2001 | Grimes | |
| 6,332,863 B1 | 12/2001 | Schweich, Jr. et al. | |
| 6,332,864 B1 | 12/2001 | Schweich, Jr. et al. | |
| 6,332,893 B1 | 12/2001 | Mortier et al. | |
| 6,355,050 B1 | 3/2002 | Andreas et al. | |
| 6,401,720 B1 | 6/2002 | Stevens et al. | |
| 6,402,679 B1 | 6/2002 | Mortier et al. | |
| 6,402,680 B2 | 6/2002 | Mortier et al. | |
| 6,402,781 B1 | 6/2002 | Langberg et al. | |
| 6,406,420 B1 | 6/2002 | McCarthy et al. | |
| 6,419,626 B1 | 7/2002 | Yoon | |
| 6,436,107 B1 | 8/2002 | Wang et al. | |
| 6,443,922 B1 | 9/2002 | Roberts et al. | |
| 6,451,054 B1 | 9/2002 | Stevens | |
| 6,461,366 B1 | 10/2002 | Seguin | |
| 6,508,777 B1 | 1/2003 | Macoviak et al. | |
| 6,514,194 B2 | 2/2003 | Schweich, Jr. et al. | |
| 6,533,796 B1 | 3/2003 | Sauer et al. | |
| 6,537,198 B1 | 3/2003 | Vidlund et al. | |
| 6,537,314 B2 | 3/2003 | Langberg et al. | |
| 6,551,331 B2 | 4/2003 | Nobles et al. | |
| 6,558,416 B2 | 5/2003 | Cosgrove et al. | |
| 6,562,052 B2 | 5/2003 | Nobles et al. | |
| 6,564,805 B2 | 5/2003 | Garrison et al. | |
| 6,582,388 B1 | 6/2003 | Coleman et al. | |
| 6,585,727 B1 | 7/2003 | Cashman et al. | |
| 6,589,160 B2 | 7/2003 | Schweich, Jr. et al. | |
| 6,602,288 B1 | 8/2003 | Cosgrove et al. | |
| 6,616,684 B1 | 9/2003 | Vidlund et al. | |
| 6,619,291 B2 | 9/2003 | Hlavka et al. | |
| 6,622,730 B2 | 9/2003 | Ekvall et al. | |
| 6,626,917 B1 | 9/2003 | Craig | |
| 6,626,930 B1 | 9/2003 | Allen et al. | |
| 6,629,534 B1 | 10/2003 | St. Goar et al. | |
| 6,629,921 B1 | 10/2003 | Schweich, Jr. et al. | |
| 6,629,984 B1 | 10/2003 | Chan | |
| 6,645,205 B2 | 11/2003 | Ginn | |
| 6,679,268 B2 | 1/2004 | Stevens et al. | |
| 6,692,605 B2 | 2/2004 | Kerr et al. | |
| 6,695,866 B1 | 2/2004 | Kuehn et al. | |
| 6,709,456 B2 | 3/2004 | Langberg et al. | |
| 6,718,985 B2 | 4/2004 | Hlavka et al. | |
| 6,723,038 B1 | 4/2004 | Schroeder et al. | |
| 6,733,509 B2 | 5/2004 | Nobles et al. | |
| 6,740,107 B2 | 5/2004 | Loeb et al. | |
| 6,743,239 B1 | 6/2004 | Kuehn et al. | |
| 6,746,471 B2 | 6/2004 | Mortier et al. | |
| 6,752,713 B2 | 6/2004 | Johnson, Jr. | |
| 6,752,813 B2 | 6/2004 | Goldfarb et al. | |
| 6,755,777 B2 | 6/2004 | Schweich, Jr. et al. | |
| 6,764,510 B2 | 7/2004 | Vidlund et al. | |
| 6,770,083 B2 | 8/2004 | Seguin | |
| 6,770,084 B1 | 8/2004 | Bain et al. | |
| 6,793,618 B2 | 9/2004 | Schweich, Jr. et al. | |
| 6,802,860 B2 | 10/2004 | Cosgrove et al. | |
| 6,808,488 B2 | 10/2004 | Mortier et al. | |
| 6,810,882 B2 | 11/2004 | Langberg et al. | |
| 6,840,246 B2 | 1/2005 | Downing | |
| 6,858,003 B2 | 2/2005 | Evans et al. | |
| 6,875,224 B2 | 4/2005 | Grimes | |
| 6,893,448 B2 | 5/2005 | O'Quinn et al. | |

(56) References Cited

U.S. PATENT DOCUMENTS

| | | | |
|---|---|---|---|
| 6,896,686 B2 | 5/2005 | Weber | |
| 6,908,424 B2 | 6/2005 | Mortier et al. | |
| 6,918,917 B1 | 7/2005 | Nguyen et al. | |
| 6,921,407 B2 | 7/2005 | Nguyen et al. | |
| 6,929,715 B2 | 8/2005 | Fladda et al. | |
| 6,936,054 B2 | 8/2005 | Chu | |
| 6,955,175 B2 | 10/2005 | Stevens et al. | |
| 6,962,605 B2 | 11/2005 | Cosgrove et al. | |
| 6,978,176 B2 | 12/2005 | Lattouf | |
| 6,986,775 B2 | 1/2006 | Morales et al. | |
| 6,989,028 B2 | 1/2006 | Lashinski et al. | |
| 6,991,635 B2 | 1/2006 | Takamoto et al. | |
| 6,997,950 B2 | 2/2006 | Chawla | |
| 7,004,176 B2 | 2/2006 | Lau | |
| 7,004,952 B2 | 2/2006 | Nobles et al. | |
| 7,011,669 B2 | 3/2006 | Kimblad | |
| 7,044,905 B2 | 5/2006 | Vidlund et al. | |
| 7,048,754 B2 | 5/2006 | Martin et al. | |
| 7,077,862 B2 | 7/2006 | Vidlund et al. | |
| 7,083,628 B2 | 8/2006 | Bachman | |
| 7,083,638 B2 | 8/2006 | Foerster | |
| 7,090,686 B2 | 8/2006 | Nobles et al. | |
| 7,094,244 B2 | 8/2006 | Schreck | |
| 7,100,614 B2 | 9/2006 | Stevens et al. | |
| 7,112,207 B2 | 9/2006 | Allen et al. | |
| 7,112,219 B2 | 9/2006 | Vidlund et al. | |
| 7,115,110 B2 | 10/2006 | Frazier et al. | |
| 7,118,583 B2 | 10/2006 | O'Quinn et al. | |
| 7,122,040 B2 | 10/2006 | Hill et al. | |
| 7,179,291 B2 | 2/2007 | Rourke et al. | |
| 7,186,264 B2 | 3/2007 | Liddicoat et al. | |
| 7,189,199 B2 | 3/2007 | McCarthy et al. | |
| 7,217,240 B2 | 5/2007 | Snow | |
| 7,226,467 B2 | 6/2007 | Lucatero et al. | |
| 7,247,134 B2 | 7/2007 | Vidlund et al. | |
| 7,250,028 B2 | 7/2007 | Julian et al. | |
| 7,288,097 B2 | 10/2007 | Seguin | |
| 7,294,148 B2 | 11/2007 | McCarthy | |
| 7,381,210 B2 | 6/2008 | Zarbatany et al. | |
| 7,464,712 B2 | 12/2008 | Oz et al. | |
| 7,563,267 B2 | 7/2009 | Goldfarb et al. | |
| 7,563,273 B2 | 7/2009 | Goldfarb et al. | |
| 7,604,646 B2 | 10/2009 | Goldfarb et al. | |
| 7,608,091 B2 | 10/2009 | Goldfarb et al. | |
| 7,635,386 B1 | 12/2009 | Gammie | |
| 7,666,204 B2 | 2/2010 | Thornton et al. | |
| 7,815,654 B2 | 10/2010 | Chu | |
| 7,879,048 B2 | 2/2011 | Bain et al. | |
| 7,887,552 B2 | 2/2011 | Bachman | |
| 8,465,500 B2 | 6/2013 | Speziali | |
| 8,545,551 B2 | 10/2013 | Loulmet | |
| 8,758,393 B2* | 6/2014 | Zentgraf | A61B 17/0469 606/207 |
| 8,968,338 B2 | 3/2015 | Speziali | |
| 9,044,221 B2 | 6/2015 | Zengraf et al. | |
| 9,192,374 B2 | 11/2015 | Zentgraf | |
| 9,364,213 B2 | 6/2016 | Speziali | |
| 9,572,556 B2 | 2/2017 | Skinlo et al. | |
| 9,700,300 B2 | 7/2017 | Speziali | |
| 10,582,924 B2 | 3/2020 | Speziali | |
| 10,588,620 B2* | 3/2020 | Caffes | A61B 17/00234 |
| 2001/0005787 A1 | 6/2001 | Oz | |
| 2001/0016675 A1 | 8/2001 | Mortier et al. | |
| 2001/0021872 A1 | 9/2001 | Bailey et al. | |
| 2002/0013571 A1 | 1/2002 | Goldfarb et al. | |
| 2002/0020732 A1* | 2/2002 | Adams | A61B 17/072 227/180.1 |
| 2002/0029080 A1 | 3/2002 | Mortier et al. | |
| 2002/0049402 A1 | 4/2002 | Peacock, III | |
| 2002/0077524 A1 | 6/2002 | Schweich, Jr. | |
| 2002/0091382 A1* | 7/2002 | Hooven | A61B 18/14 606/41 |
| 2002/0169359 A1 | 11/2002 | McCarthy | |
| 2002/0173694 A1 | 11/2002 | Mortier et al. | |
| 2002/0183766 A1 | 12/2002 | Seguin | |
| 2002/0183787 A1 | 12/2002 | Wahr et al. | |
| 2003/0004562 A1 | 1/2003 | DiCarlo | |
| 2003/0032979 A1 | 2/2003 | Mortier et al. | |
| 2003/0050529 A1 | 3/2003 | Vidlund et al. | |
| 2003/0050693 A1 | 3/2003 | Quijano | |
| 2003/0078599 A1 | 4/2003 | O'Quinn et al. | |
| 2003/0078600 A1 | 4/2003 | O'Quinn et al. | |
| 2003/0105519 A1 | 6/2003 | Fasol | |
| 2003/0120341 A1 | 6/2003 | Shennib et al. | |
| 2003/0130731 A1 | 7/2003 | Vidlund et al. | |
| 2003/0163029 A1 | 8/2003 | Sonnenschein et al. | |
| 2003/0166992 A1 | 9/2003 | Schweich, Jr. | |
| 2003/0167071 A1 | 9/2003 | Martin et al. | |
| 2003/0171641 A1 | 9/2003 | Schweich, Jr. | |
| 2003/0181928 A1 | 9/2003 | Vidlund et al. | |
| 2003/0187457 A1 | 10/2003 | Weber | |
| 2003/0195529 A1 | 10/2003 | Takamoto et al. | |
| 2003/0199975 A1 | 10/2003 | Gabbay | |
| 2004/0003819 A1 | 1/2004 | St. Goar | |
| 2004/0030382 A1 | 2/2004 | St. Goar | |
| 2004/0039442 A1 | 2/2004 | St. Goar | |
| 2004/0044350 A1 | 3/2004 | Martin et al. | |
| 2004/0044365 A1 | 3/2004 | Bachman | |
| 2004/0049207 A1 | 3/2004 | Goldfarb et al. | |
| 2004/0049552 A1 | 3/2004 | Motoyama | |
| 2004/0087975 A1 | 5/2004 | Lucatero et al. | |
| 2004/0087978 A1 | 5/2004 | Velez et al. | |
| 2004/0092962 A1 | 5/2004 | Thornton et al. | |
| 2004/0097805 A1 | 5/2004 | Verard et al. | |
| 2004/0116767 A1 | 6/2004 | Lebovic | |
| 2004/0122448 A1 | 6/2004 | Levine | |
| 2004/0127983 A1 | 7/2004 | Mortier et al. | |
| 2004/0133063 A1 | 7/2004 | McCarthy et al. | |
| 2004/0167374 A1 | 8/2004 | Schweich et al. | |
| 2004/0167539 A1 | 8/2004 | Kuehn et al. | |
| 2004/0225300 A1 | 11/2004 | Goldfarb et al. | |
| 2004/0225304 A1 | 11/2004 | Vidlund et al. | |
| 2004/0236353 A1 | 11/2004 | Bain et al. | |
| 2004/0236354 A1 | 11/2004 | Seguin | |
| 2004/0236373 A1 | 11/2004 | Anspach, III | |
| 2004/0243229 A1 | 12/2004 | Vidlund et al. | |
| 2004/0267083 A1 | 12/2004 | McCarthy | |
| 2005/0004668 A1 | 1/2005 | Aklog et al. | |
| 2005/0021055 A1 | 1/2005 | Toubia et al. | |
| 2005/0021056 A1 | 1/2005 | St. Goar | |
| 2005/0021057 A1 | 1/2005 | St. Goar | |
| 2005/0033446 A1 | 2/2005 | Deem et al. | |
| 2005/0065396 A1 | 3/2005 | Mortier et al. | |
| 2005/0075723 A1 | 4/2005 | Schroeder et al. | |
| 2005/0075727 A1 | 4/2005 | Wheatley | |
| 2005/0101975 A1 | 5/2005 | Nguyen et al. | |
| 2005/0125011 A1 | 6/2005 | Spence et al. | |
| 2005/0131277 A1 | 6/2005 | Schweich, Jr. | |
| 2005/0131533 A1 | 6/2005 | Alfieri et al. | |
| 2005/0143620 A1 | 6/2005 | Mortier et al. | |
| 2005/0148815 A1 | 7/2005 | Mortier et al. | |
| 2005/0149014 A1 | 7/2005 | Hauck et al. | |
| 2005/0154402 A1 | 7/2005 | Sauer et al. | |
| 2005/0165419 A1 | 7/2005 | Sauer et al. | |
| 2005/0171601 A1 | 8/2005 | Cosgrove | |
| 2005/0216039 A1 | 9/2005 | Lederman | |
| 2005/0240202 A1 | 10/2005 | Shennib et al. | |
| 2005/0251187 A1 | 11/2005 | Beane et al. | |
| 2006/0020275 A1 | 1/2006 | Goldfarb et al. | |
| 2006/0036317 A1 | 2/2006 | Vidlund et al. | |
| 2006/0041306 A1 | 2/2006 | Vidlund et al. | |
| 2006/0052868 A1 | 3/2006 | Mortier et al. | |
| 2006/0058871 A1 | 3/2006 | Zakay et al. | |
| 2006/0074484 A1 | 4/2006 | Huber | |
| 2006/0074485 A1 | 4/2006 | Realyvasquez | |
| 2006/0089671 A1 | 4/2006 | Goldfarb et al. | |
| 2006/0100699 A1 | 5/2006 | Vidlund et al. | |
| 2006/0127509 A1 | 6/2006 | Eckman | |
| 2006/0135993 A1 | 6/2006 | Seguin | |
| 2006/0149123 A1 | 7/2006 | Vidlund et al. | |
| 2006/0161040 A1 | 7/2006 | McCarthy | |
| 2006/0161193 A1 | 7/2006 | Beane et al. | |
| 2006/0184203 A1 | 8/2006 | Martin et al. | |
| 2006/0195012 A1 | 8/2006 | Mortier et al. | |

(56) References Cited

U.S. PATENT DOCUMENTS

| | | |
|---|---|---|
| 2006/0195134 A1 | 8/2006 | Crittenden |
| 2006/0195183 A1 | 8/2006 | Navia et al. |
| 2006/0241340 A1 | 10/2006 | Vidlund |
| 2006/0287657 A1 | 12/2006 | Bachman |
| 2007/0002627 A1 | 1/2007 | Youn |
| 2007/0027451 A1 | 2/2007 | Desinger et al. |
| 2007/0049952 A1 | 3/2007 | Weiss |
| 2007/0050022 A1 | 3/2007 | Vidlund et al. |
| 2007/0055303 A1 | 3/2007 | Vidlund et al. |
| 2007/0088375 A1 | 4/2007 | Beane et al. |
| 2007/0100356 A1 | 5/2007 | Lucatero et al. |
| 2007/0112244 A1 | 5/2007 | McCarthy |
| 2007/0118151 A1 | 5/2007 | Davidson |
| 2007/0118154 A1 | 5/2007 | Crabtree |
| 2007/0118155 A1 | 5/2007 | Goldfarb et al. |
| 2007/0118213 A1 | 5/2007 | Loulmet |
| 2007/0129737 A1 | 6/2007 | Goldfarb et al. |
| 2007/0179511 A1 | 8/2007 | Paolitto |
| 2007/0197858 A1 | 8/2007 | Goldfarb et al. |
| 2007/0203391 A1 | 8/2007 | Bloom et al. |
| 2007/0232941 A1 | 10/2007 | Rabinovich |
| 2007/0239272 A1 | 10/2007 | Navia et al. |
| 2007/0265643 A1 | 11/2007 | Beane et al. |
| 2007/0299468 A1 | 12/2007 | Viola |
| 2008/0004485 A1 | 1/2008 | Moreschi |
| 2008/0027468 A1 | 1/2008 | Fenton |
| 2008/0051703 A1 | 2/2008 | Thornton et al. |
| 2008/0065011 A1 | 3/2008 | Marchand et al. |
| 2008/0065156 A1 | 3/2008 | Hauser et al. |
| 2008/0065205 A1 | 3/2008 | Nguyen et al. |
| 2008/0091059 A1 | 4/2008 | Machold |
| 2008/0091264 A1 | 4/2008 | Machold |
| 2008/0097482 A1 | 4/2008 | Bain et al. |
| 2008/0097489 A1 | 4/2008 | Goldfarb et al. |
| 2008/0109069 A1 | 5/2008 | Coleman et al. |
| 2008/0125860 A1 | 5/2008 | Webler et al. |
| 2008/0125861 A1 | 5/2008 | Webler et al. |
| 2008/0167714 A1 | 7/2008 | St. Goar |
| 2008/0183194 A1 | 7/2008 | Goldfarb et al. |
| 2008/0188873 A1 | 8/2008 | Speziali |
| 2008/0195200 A1 | 8/2008 | Vidlund et al. |
| 2008/0208006 A1 | 8/2008 | Farr |
| 2008/0228223 A1 | 9/2008 | Alkhatib |
| 2008/0243245 A1 | 10/2008 | Thamber et al. |
| 2009/0062819 A1* | 3/2009 | Burkhart ............ A61B 17/0469 606/148 |
| 2009/0105729 A1 | 4/2009 | Zentgraf |
| 2009/0105751 A1 | 4/2009 | Zentgraf |
| 2009/0131880 A1 | 5/2009 | Speziali et al. |
| 2009/0156995 A1 | 6/2009 | Martin et al. |
| 2009/0163934 A1 | 6/2009 | Raschdorf, Jr. |
| 2009/0192598 A1 | 7/2009 | Lattouf et al. |
| 2009/0259304 A1 | 10/2009 | O'Beirne et al. |
| 2010/0030061 A1 | 2/2010 | Canfield et al. |
| 2010/0042147 A1 | 2/2010 | Janovsky et al. |
| 2010/0160726 A1 | 6/2010 | Windheuser |
| 2010/0174297 A1 | 7/2010 | Speziali |
| 2010/0185172 A1 | 7/2010 | Fabro |
| 2010/0217283 A1 | 8/2010 | St. Goar |
| 2010/0298929 A1 | 11/2010 | Thornton et al. |
| 2011/0011917 A1 | 1/2011 | Loulmet |
| 2012/0184971 A1 | 7/2012 | Zentgraf et al. |
| 2013/0035757 A1 | 2/2013 | Zentgraf et al. |
| 2013/0150710 A1 | 6/2013 | Zentgraf et al. |
| 2014/0039324 A1 | 2/2014 | Speziali |
| 2014/0364875 A1 | 12/2014 | Zentgraf |
| 2015/0148821 A1 | 5/2015 | Speziali |
| 2017/0290582 A1 | 10/2017 | Speziali |
| 2019/0290260 A1 | 9/2019 | Caffes et al. |
| 2019/0343626 A1 | 11/2019 | Smirnov et al. |
| 2019/0343633 A1 | 11/2019 | Garvin et al. |
| 2019/0343634 A1 | 11/2019 | Garvin et al. |

FOREIGN PATENT DOCUMENTS

| | | | |
|---|---|---|---|
| EP | 1845861 | A2 | 10/2007 |
| EP | 1408850 | B1 | 9/2009 |
| JP | H 04307052 | A | 10/1992 |
| JP | 06142114 | | 5/1994 |
| JP | 2004-531337 | | 10/2004 |
| JP | 2007-535342 | | 12/2007 |
| WO | WO 1999/000059 | A1 | 1/1999 |
| WO | WO 1999/030647 | A1 | 6/1999 |
| WO | WO 2000/006026 | A2 | 2/2000 |
| WO | WO 2000/006027 | A2 | 2/2000 |
| WO | WO 2000/006028 | A1 | 2/2000 |
| WO | WO 2000/016700 | A1 | 3/2000 |
| WO | WO 2001/066018 | A1 | 9/2001 |
| WO | WO 2001/095809 | A1 | 12/2001 |
| WO | WO 2003/001893 | A2 | 1/2003 |
| WO | WO 2003/059209 | A2 | 7/2003 |
| WO | WO 2003/079937 | A2 | 10/2003 |
| WO | WO 2003/082157 | A2 | 10/2003 |
| WO | WO 2003/082158 | A1 | 10/2003 |
| WO | WO 2004/021893 | A1 | 3/2004 |
| WO | WO 2004/043265 | A2 | 5/2004 |
| WO | WO 2005/039428 | A2 | 5/2005 |
| WO | WO 2005/087140 | A1 | 9/2005 |
| WO | WO 2005/094525 | A2 | 10/2005 |
| WO | WO 2006/012750 | A1 | 2/2006 |
| WO | WO 2006/032051 | A2 | 3/2006 |
| WO | WO 2006/065966 | A2 | 6/2006 |
| WO | WO 2006/078694 | A2 | 7/2006 |
| WO | WO 2006/116310 | A2 | 11/2006 |
| WO | WO 2006/127509 | A2 | 11/2006 |
| WO | WO 2007/002627 | A1 | 1/2007 |
| WO | WO 2007/027451 | A2 | 3/2007 |
| WO | WO 2007/062128 | A2 | 5/2007 |
| WO | WO 2007/081418 | A1 | 7/2007 |
| WO | WO 2007/117612 | A1 | 10/2007 |
| WO | WO 2008/010738 | A2 | 1/2008 |
| WO | WO 2009/052528 | A2 | 4/2009 |
| WO | WO 2011/070477 | A1 | 6/2011 |
| WO | WO 2011/137336 | A1 | 11/2011 |
| WO | WO 2012/167120 | A1 | 12/2012 |

OTHER PUBLICATIONS

Interactive Cardio Vascular and Thoracic Surgery; Abstracts; Suppl 3 to vol. 7 (Sep. 2008) 52 pages.

Machine translation of JP 06142114.

Port Access System for Mitral Valve Repair Proves Its Value in Study; MedGadget Jul. 9, 2009 (2 pages).

Application and File History for U.S. Appl. No. 12/254,808, filed Oct. 20, 2008, now U.S. Pat. No. 9,192,374. Inventors: Zentgraf.

Application and File History for U.S. Appl. No. 16/678,571, filed Nov. 8, 2019. Inventor: Zentgraf.

Application and File History for U.S. Appl. No. 16/363,701, filed Mar. 25, 2019, now U.S. Pat. No. 10,588,620. Inventors: Caffes et al.

Application and File History for U.S. Appl. No. 16/818,639, filed Mar. 13, 2020. Inventors: Caffes et al.

Application and File History for U.S. Appl. No. 16/406,736 filed May 8, 2019. Inventors: Smirnov et al.

Application and File History for U.S. Appl. No. 16/406,764, filed May 8, 2019. Inventors: Garvin et al.

Application and File History for U.S. Appl. No. 16/406,799, filed May 8, 2019. Inventors: Garvin et al.

Application and File History for U.S. Appl. No. 16/745,074, filed Jan. 16, 2020. Inventors: Edmiston et al.

Application and File History for U.S. Appl. No. 14/947,399, filed Nov. 20, 2015. Inventors: Zeentgraf et al.

* cited by examiner

DEVICE FOR SUTURE ATTACHMENT FOR MINIMALLY INVASIVE HEART VALVE REPAIR

RELATED APPLICATION

This application claims the benefit of U.S. Provisional Application No. 62/728,349 filed Sep. 7, 2018, which is hereby fully incorporated herein by reference.

TECHNICAL FIELD

The disclosed invention relates to minimally invasive delivery of a suture. More particularly, the disclosed invention relates to attaching the suture as an artificial chordae tendineae to a flailing or prolapsing leaflet in a beating heart.

BACKGROUND

The mitral and tricuspid valves inside the human heart include an orifice (annulus), two (for the mitral) or three (for the tricuspid) leaflets and a subvalvular apparatus. The subvalvular apparatus includes multiple chordae tendineae, which connect the mobile valve leaflets to muscular structures (papillary muscles) inside the ventricles. Rupture or elongation of the chordae tendineae results in partial or generalized leaflet prolapse, which causes mitral (or tricuspid) valve regurgitation. A commonly used technique to surgically correct mitral valve regurgitation is the implantation of artificial chordae (usually 4-0 or 5-0 Gore-Tex sutures) between the prolapsing segment of the valve and the papillary muscle.

This procedure was traditionally an open heart operation generally carried out through a median sternotomy and requiring cardiopulmonary bypass with aortic cross-clamp and cardioplegic arrest of the heart. Using such open heart techniques, the large opening provided by a median sternotomy or right thoracotomy enables the surgeon to see the mitral valve directly through the left atriotomy, and to position his or her hands within the thoracic cavity in close proximity to the exterior of the heart for manipulation of surgical instruments, removal of excised tissue, and/or introduction of an artificial chordae through the atriotomy for attachment within the heart. However, these invasive open heart procedures produce a high degree of trauma, a significant risk of complications, an extended hospital stay, and a painful recovery period for the patient. Moreover, while heart valve surgery produces beneficial results for many patients, numerous others who might benefit from such surgery are unable or unwilling to undergo the trauma and risks of such open heart techniques.

Techniques for minimally invasive thoracoscopic repair of heart valves while the heart is still beating have also been developed. U.S. Pat. No. 8,465,500 to Speziali, which is incorporated by reference herein, discloses a thoracoscopic heart valve repair method and apparatus. Instead of requiring open heart surgery on a stopped heart, the thoracoscopic heart valve repair methods and apparatus taught by Speziali utilize fiber optic technology in conjunction with transesophageal echocardiography (TEE) as a visualization technique during a minimally invasive surgical procedure that can be utilized on a beating heart. More recent versions of these techniques are disclosed in U.S. Pat. Nos. 8,758,393 and 9,192,374 to Zentgraf, which disclose an integrated device that can enter the heart chamber, navigate to the leaflet, capture the leaflet, confirm proper capture, and deliver a suture as part of a mitral valve regurgitation (MR) repair. These minimally invasive repairs are generally performed through a small, between the ribs access point, followed by a puncture into the ventricle through the apex of the heart. Although far less invasive and risky for the patient than an open heart procedure, these thoracoscopic procedures are still involving significant recovery time and pain.

It would be advantageous for a minimally invasive suture delivery system to be able to suture valve leaflets in a beating heart procedure without requiring an open surgical approach or an incision into the exterior ventricular wall of a minimally invasive thoracoscopic approach in order to minimize blood loss and reduce recovery time and pain. For example, various approaches to heart valve repair using intravascular access have been proposed, including U.S. Patent Publication Nos. 2007/0118151 and 2013/0035757 and U.S. Pat. Nos. 7,635,386, 8,043,368 and 8,545,551. These approaches, however, have not resolved various issues with respect to a successful intravascular technique that could match the results of open heart or thoracoscopic techniques, including the known challenges of effectively grasping and retaining the beating leaflets during a beating heart intravascular procedure.

SUMMARY

Disclosed herein are minimally invasive systems and methods for intravascularly accessing the heart and performing a transcatheter repair of a heart valve by inserting a suture as an artificial chordae into a heart valve leaflet. In various embodiments, such systems and methods can be employed in other heart valve repair procedures such an edge to edge repair to coapt leaflets by inserting one or more sutures that retain the leaflets in a coapted positioned or inserting a suture to repair a tear in a leaflet, for example.

In an embodiment, a suture attachment catheter configured to repair a heart valve by inserting a suture in a valve leaflet of a beating heart of a patient can include a generally flexible catheter body, a suture attachment assembly, and a control handle. The suture attachment assembly can include a proximal clamping jaw, a rail selectively slideable with respect to the proximal clamping jaw and a distal clamping jaw hingedly attached to the distal end of the rail. The control handle can include a rail actuator configured to selectively longitudinally slide the rail with respect to the proximal clamping jaw and a jaw actuator configured to selectively pivot the distal clamping jaw between a first position for delivery of the suture attachment assembly into the heart and a second position for capturing a valve leaflet between the proximal clamping jaw and the distal clamping jaw. In embodiments, a flexible member extends from the jaw actuator through the catheter body to a distal surface of the distal clamping jaw and is selectively moved to pivot the distal clamping jaw.

Various embodiments of systems, devices and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

BRIEF DESCRIPTION OF THE DRAWINGS

The invention may be more completely understood in consideration of the following detailed description of various embodiments of the invention in connection with the accompanying drawings, in which.

Figure 1A:
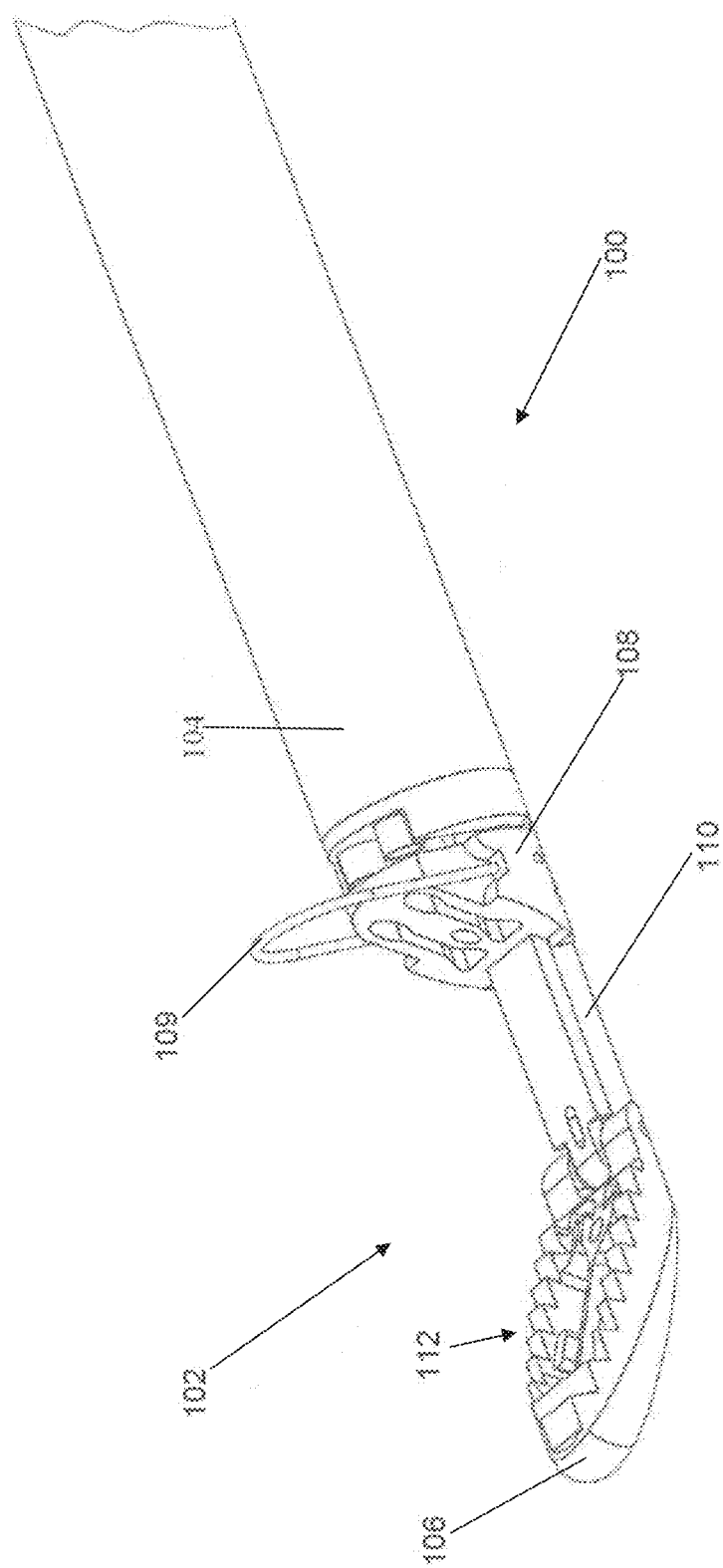
FIGS. 1A-1C depict a distal end of a suture attachment device according to an embodiment.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present application describes various devices and methods that can be employed on the beating heart of a patient in a minimally invasive manner to treat mitral valve regurgitation as described above. Embodiments as described herein can be used to restrain a prolapsing leaflet to prevent leaflet prolapse and to promote leaflet coaptation. In other embodiments, such systems and methods can be employed in other heart valve repair procedures such an edge to edge repair to coapt leaflets by inserting one or more sutures that retain the leaflets in a coapted positioned or inserting a suture to repair a tear in a leaflet, for example.

Figure 1B:
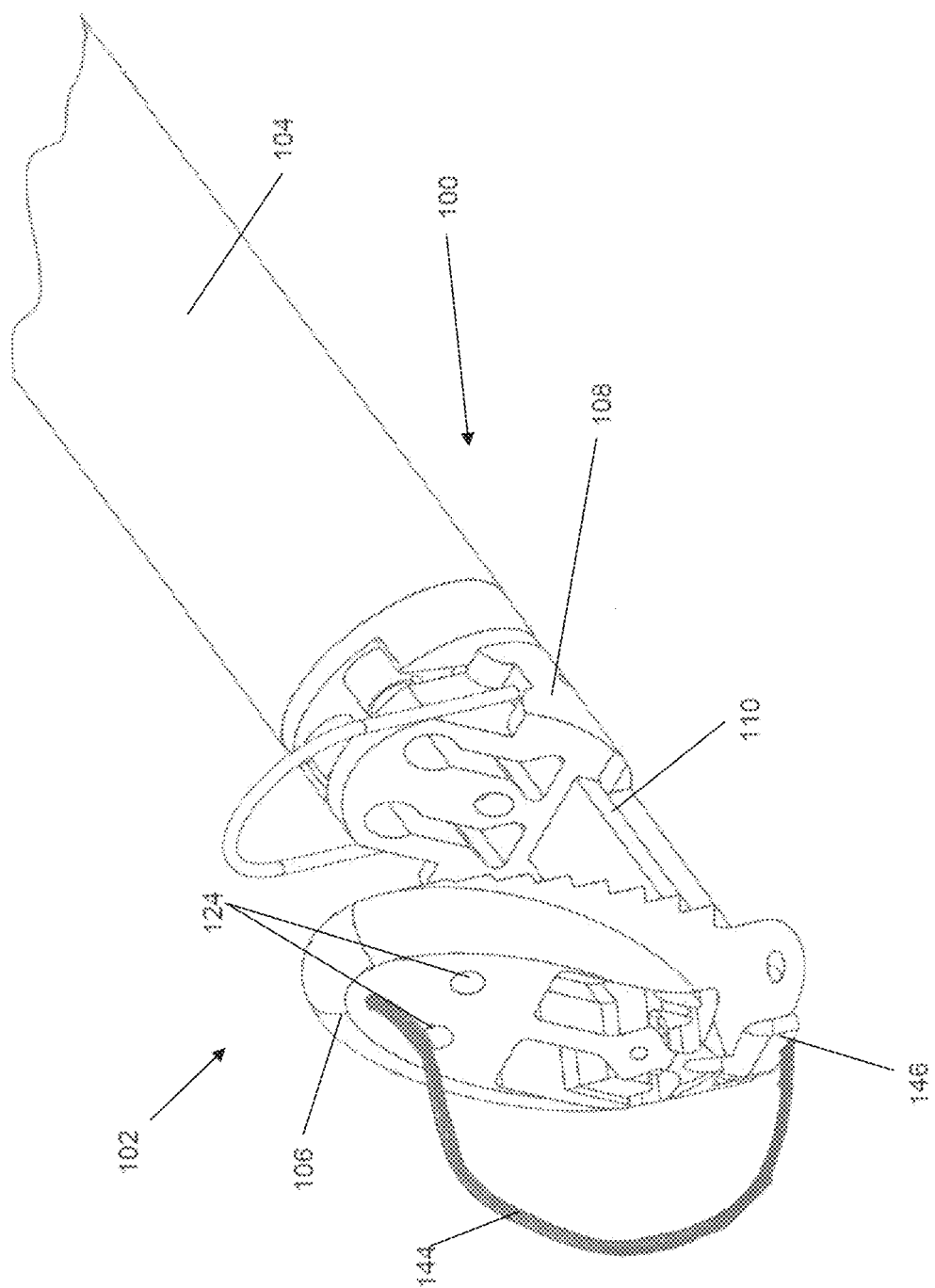
Figure 1C:
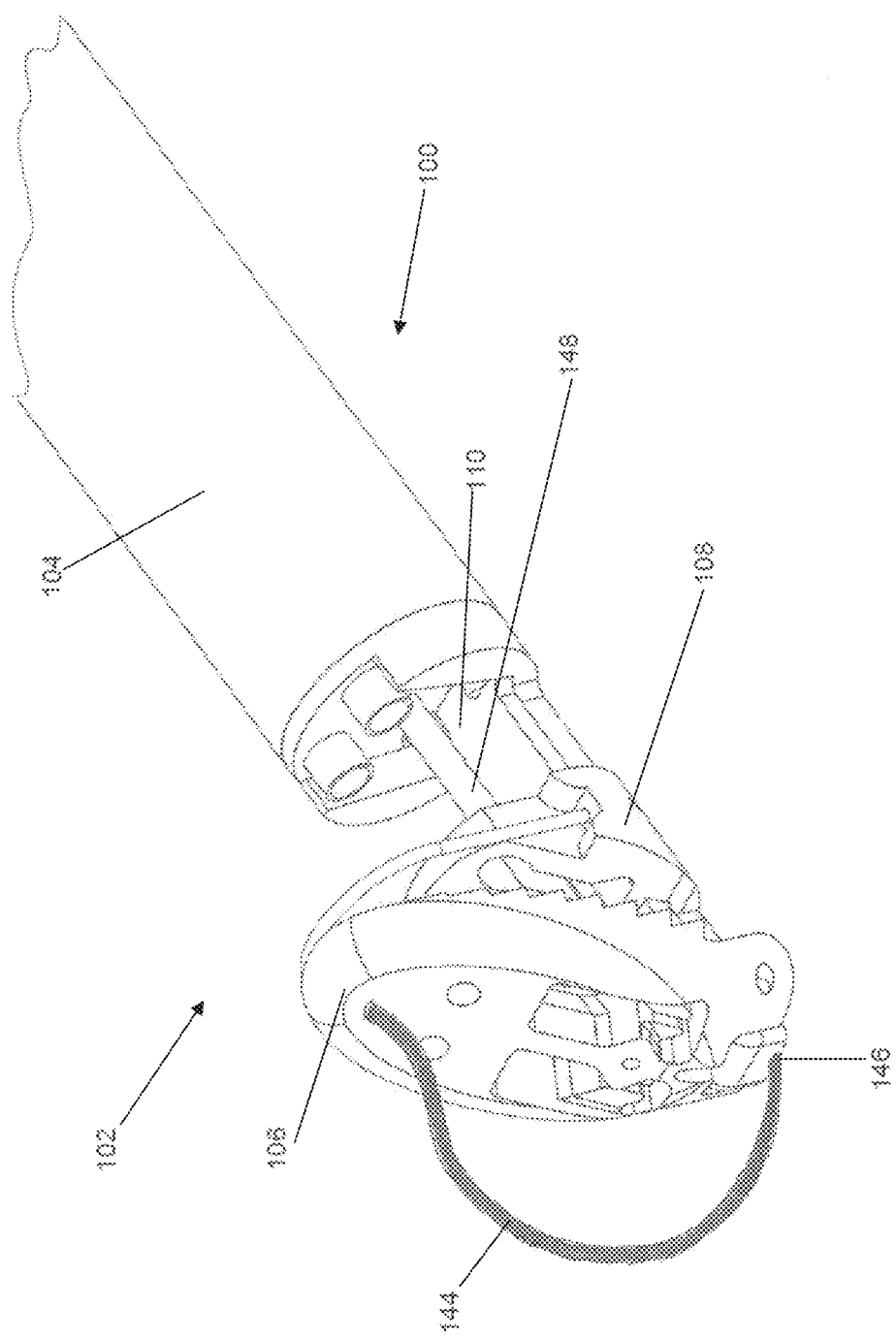

FIGS. 1A-1C depict a distal end 102 of a suture attachment device 100 according to an embodiment. Suture attachment device 100 can be configured as leaflet attachment catheter with the distal end 102 being the distal capture portion of the leaflet attachment catheter. In embodiments, the catheter is configured to enter the patient through a delivery sheath which is inserted at the groin, extends through the inferior vena cava to the right atrium and then through a transeptal puncture into the left atrium. The catheter has a shaft or body 104 of a length to extend through the delivery sheath while allowing the distal end 102 to extend distal to the distal end of the delivery sheath within the patient while also extending proximally to the proximal end of the delivery sheath at the proximal end of the catheter allowing the physician to access the control handle attached to the proximal end of the catheter. In such an embodiment, the catheter body 104 can be flexible.

In embodiments, the total working length of the catheter body can be between about 130 cm and 140 cm. On a typical patient, this length enables the catheter to be advanced into the heart from the groin with additional length for the delivery system catheters and control handles. The catheter can be flexible and configured to be able to flex around a curve having a diameter between 0.75 inches and 1.5 inches, such as, for example, a 0.9 inch diameter curve, depending on the septal puncture location and the specific anatomy of the patient. In other embodiments, the total working length can be between about 100 cm and 170 cm in order to accommodate very short or very tall patients.

In embodiments, the working length of the distal end 102 of the device advanced out of the delivery system can be between about 3 cm and 6 cm. The distal end 102 can be generally rigid, but provided with some flexibility as the device is advanced through the delivery system by a hinged distal jaw as will be described herein. This flexibility enables the distal end to traverse curves on the range of 0.75 inches to 1.5 inches within the internal diameter of the delivery system which, in some embodiments, may be approximately 5-6 mm.

In embodiments, catheter shaft or body is comprised of a combination of stainless steel braid and coil reinforced nylon or polyurethane to provide axial and torsional rigidity along with flexibility. The components of the distal end, such as the clamping jaws as will be described herein, can be comprised of, for example, medical grade polymers or machined stainless steel.

The distal end 102 of the catheter 100 includes a distal jaw 106 and a proximal jaw 108 and mechanisms that actuate the jaws between their respective positions depending on the portion of the procedure being done, as will be described herein. Distal jaw 106 is hingedly attached to a rail 110. Proximal jaw 108 is selectively slideable along rail 110 and can include a loop 109 configured as a wire extending upwardly therefrom. In embodiments, wire loop 109 can be formed from a shape memory material such as, e.g., nitinol. In operation, distal jaw 106 can selectively be actuated between a first position shown in FIG. 1A and a second position shown in FIGS. 1B-1C. Proximal jaw 108 can selectively slide along rail 110 between a first, proximal position depicted in FIGS. 1A-1B and second, distal position depicted in FIG. 1C. In another embodiment, the proximal jaw 108 can be fixed in its axial movement and the rail 110 with the distal jaw 106 attached can slide distally from a first position with respect to the fixed proximal jaw to a second position to effectively increase the distance between the proximal jaw and the distal jaw.

Figure 2A:
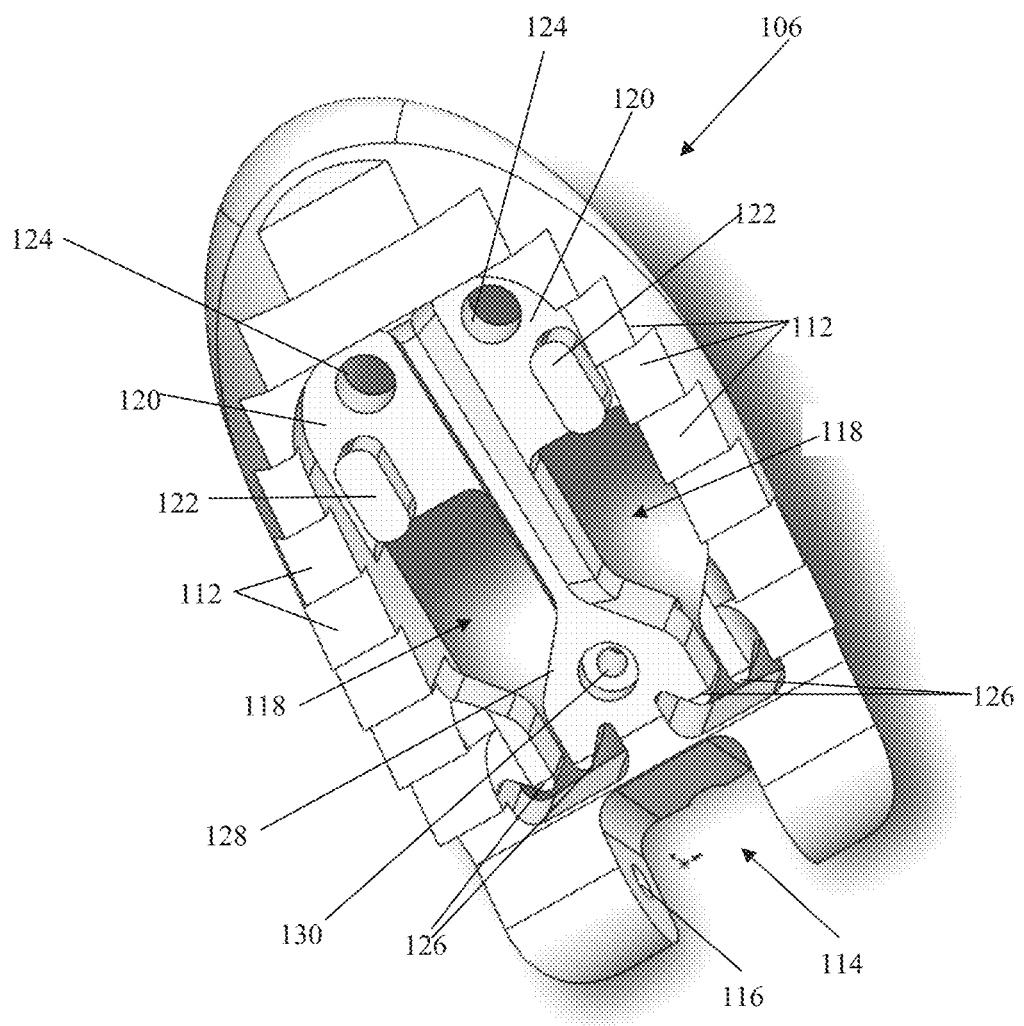
FIGS. 2A-2B depict a distal jaw of the suture attachment device of FIGS. 1A-1C.
Figure 2B:
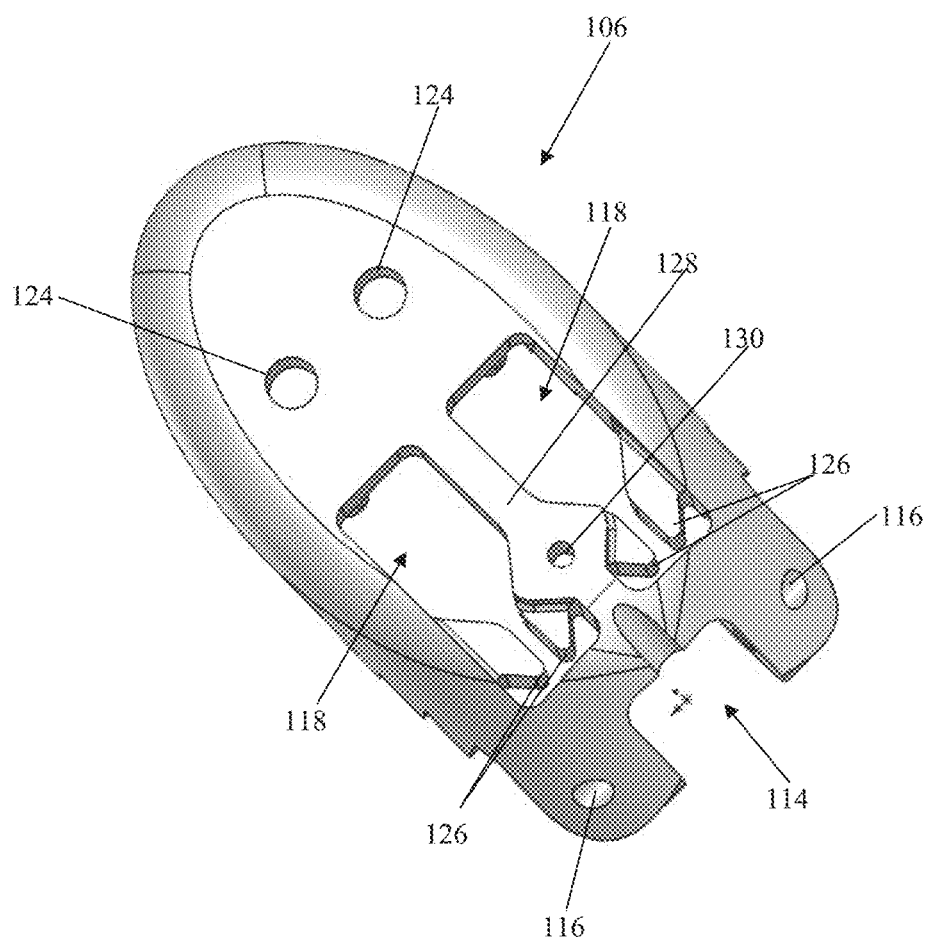

Referring now also to FIG. 2A-2B, further details regarding the distal jaw 106 according to an embodiment will be described. Distal jaw 106 includes a leaflet clamping surface having a plurality of stepped ridges 112 configured to enhance the ability of the jaws to clamp and retain a valve leaflet. Distal jaw 106 further includes a rail opening 114 and a pair of aligned apertures 116 extending through distal jaw 106. Rail opening 114 is configured to receive a distal end of rail 110 (see FIG. 1A) with the apertures 116 configured to receive a pin, rod, etc. that extends through a corresponding aperture in rail 110 to form the hinged attachment between distal jaw 106 and rail 110. Distal jaw 106 further includes a pair of clamping face openings 118. A portion of clamping face openings 118 extends completely through the distal jaw 106 whereas another portion extends only partway through due to the presence of ledges 120. A distal post 122 extends upwardly from and a distal aperture 124 extends through each ledge 120. Clamping face openings 118 further each define a pair of intermediate tabs 126. A recessed opening 130 also extends through a ledge 128 extending between the openings 118.

Figure 3:
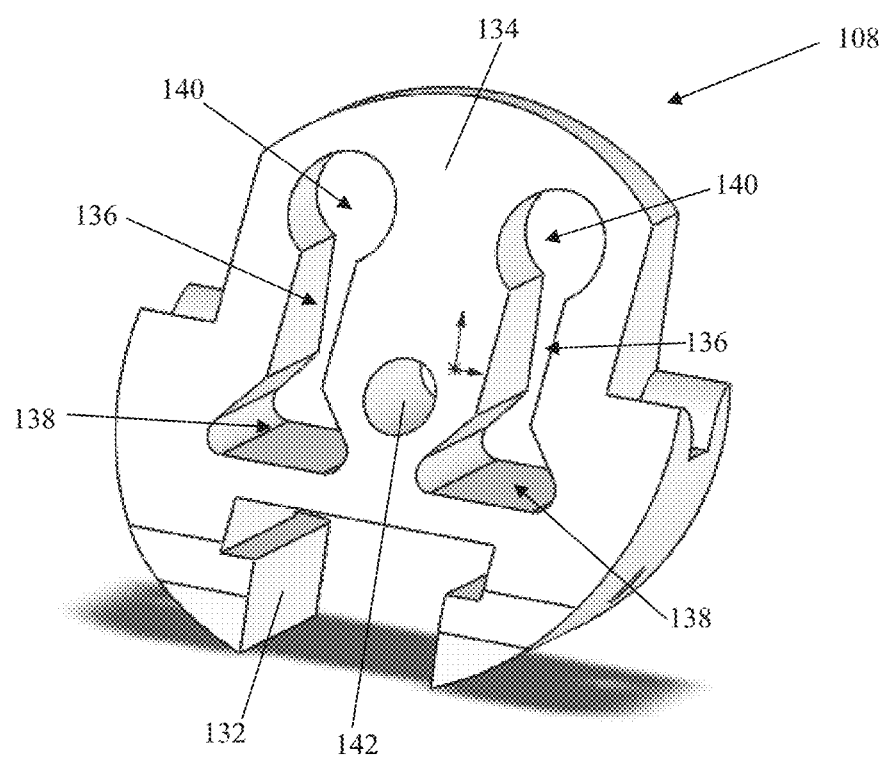
FIG. 3 depicts a proximal clamping jaw of the suture attachment device of FIGS. 1A-1C.

Referring now to FIG. 3, further details regarding an embodiment of a proximal clamping jaw 108 are depicted. Proximal jaw 108 includes a rail opening 132 that conforms to a shape of the rail 110 (see FIG. 1A) to enable proximal jaw 108 to selectively slide along rail 110. Proximal jaw 108 further includes a distal clamping face 134 having a pair of elongate slots 136 therethrough. Elongate slots 136 each define both a suture slot 138 and a needle hole 140. An actuator aperture 142 is further defined through proximal jaw 108.

As noted above, and with reference again to FIGS. 1A-1C, distal jaw 106 can be actuated between at least two positions. The first, delivery position is depicted in FIG. 1A and includes the distal jaw 106 being positioned at an obtuse angle (i.e., an angle between 90 and 180 degrees) relative to the rail 110. In the depicted embodiment, the distal jaw 106 is positioned approximately 120 degrees relative to the rail. The delivery position is the configuration in which the distal end 102 is delivered through the delivery system to the point of use (i.e., adjacent a valve leaflet). The second, clamping position is depicted in FIGS. 1B-1C and includes the distal jaw 106 positioned at a right angle or acute angle (less than 90 degrees) relative to the rail 110. In the depicted embodiment, the distal jaw 106 has been actuated approximately 90 degrees relative to the first position, such that the jaw 106 is positioned at an approximately 60 degree angle relative to the rail 110. The clamping position is the position the distal jaw 106 is moved to when the jaw 106 has been positioned inferior to a leaflet to enable to jaw surface to contact and stabilize the leaflet for capture of the leaflet.

Actuation of the distal jaw 106 between the delivery position and the clamping position is accomplished with a flexible member 144. In embodiments, flexible member 144 can be a nitinol wire. Flexible member 144 can extend through a lumen 146 through the catheter shaft or body 104 and the rail 110 and exits lumen 146 at a distal face of the rail 110. The distal end of the flexible member 144 attaches to the distal jaw 106. Although not depicted as such in FIGS. 1B-1C, in embodiments the flexible member 144 can be attached to the distal jaw 106 via one or more of distal apertures 124. When this flexible member 144 is further extended from the lumen 146, its connection to the distal jaw 106 moves the jaw from the first, delivery position in which it is delivered to the second, clamping position in which is able to contact the inferior surface of the valve leaflet. The distal jaw 106 can be moved back to the delivery position by pulling on the flexible member 144. Flexible member 144 can be controlled with sliding movement of an actuator disposed at a proximal end of the device.

The proximal jaw 108 is actuated with a flexible proximal jaw actuator rod 148, as shown in FIG. 1C, that connects to the actuator aperture 142 of the proximal jaw 108. The actuator rod 148 can be pushed moved an actuator control at the proximal end of the device to advance the proximal jaw 108 along the rail 110 to close the distance between the proximal jaw 108 and the distal jaw 106 to clamp a leaflet therebetween. Wire loop 109 on proximal jaw 108 is configured to approximately mate (on opposite sides of the leaflet) with the distal jaw 106 when both jaws have been actuated to the clamping position. When the proximal jaw 108 is advanced to the actuated distal jaw 106 with the valve leaflet between them, it will provide pressure to stabilize the leaflet between the jaws while minimizing potential damage to the leaflet. In some embodiments, distal clamping face of proximal jaw 108 can be angled to match the angle of distal jaw 106 in the clamping position (i.e., approximately 60 degrees in the depicted embodiment).

The above-described jaw configuration provides a number of advantages. One advantage is that it allows for relatively large surface areas to be included in the clamping portion of the jaw by providing for a first configuration in which the larger distal jaw can more easily be delivered and a second, different configuration in which the larger jaw is employed to capture and retain a leaflet. Another advantage is that the hinged connection reduces the rigid length of the device while still allowing a large jaw opening distance. It does this by allowing the hinged distal jaw to flex as needed while the system is advanced through the small radius that is required for delivery to the mitral valve through the vasculature and a septal puncture.

Figure 4A:
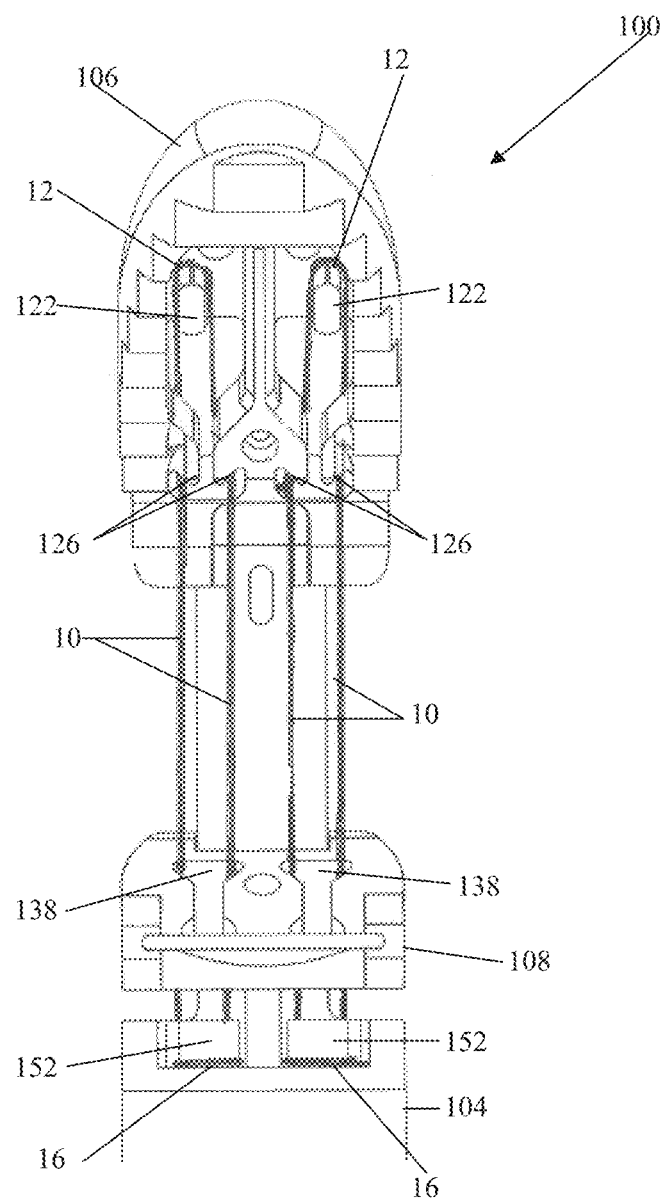
FIGS. 4A-4B depict schematic representations of the routing of one or more sutures through a suture attachment device according to an embodiment.
Figure 4B:
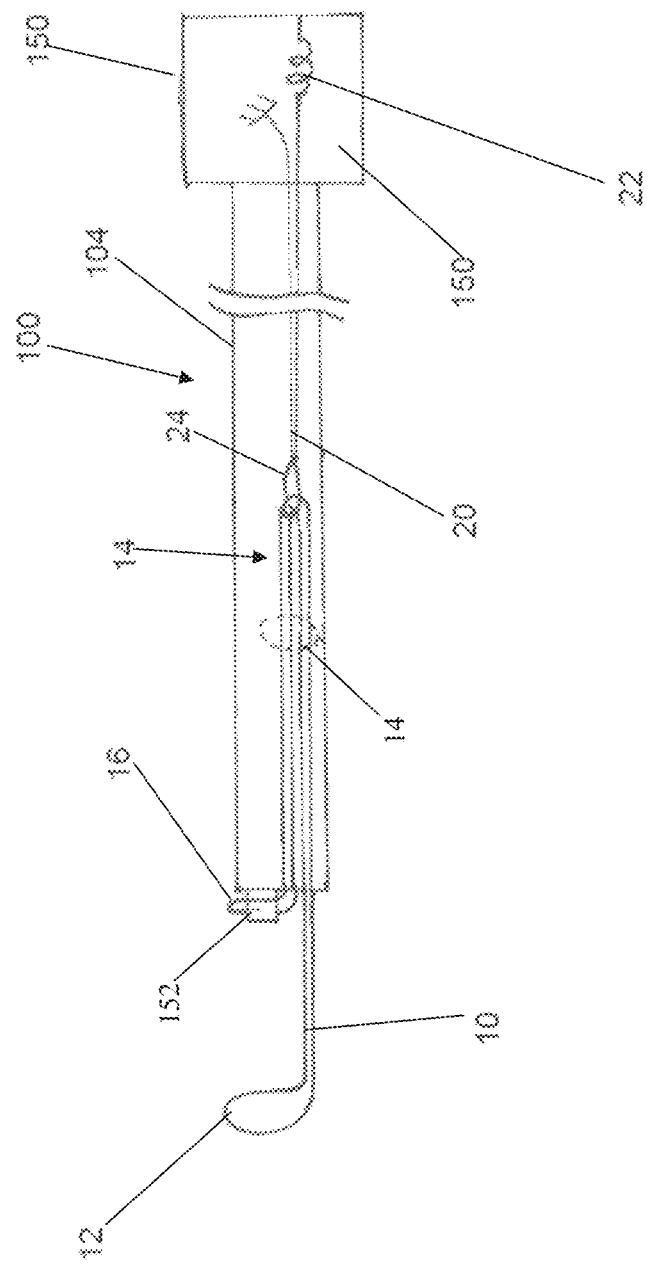

FIGS. 4A-4B depict schematic representations of an embodiment of a manner in which one or more sutures can be routed through the device 100. FIG. 4B depicts device without the proximal jaw 108 and distal jaw 106 as well as a single suture 10 for sake of clarity. FIG. 4A depicts a pair of sutures 10 carried side by side in device 100. Because each suture is routed through device in an identical but side by side manner, only the routing of a single suture 10 will be described in detail. In embodiments, one or more sutures can be preinstalled in the catheter prior to delivery to the end user (i.e., surgeon).

Suture 10 can be configured in a continuous loop through device 100. The routing of the suture 10 through the distal jaw is done by securing a first distal end suture loop 12 portion around the distal post 122 on the leaflet clamping surface side of the distal jaw 106. The suture 10 then extends from both sides of the post and around the opposite side of the intermediate tabs 126 in the distal clamping jaw 106, through the suture slots 138 in the proximal jaw 108 and then into a suture channel extending through the catheter body 104. Within each suture channel of the catheter body 104, both legs of the suture 10 are doubled with the resulting proximal double loop 14 of suture 10 being held with a separate looped suture 20 which is connected within the proximal control handle 150 by a spring 22 to keep tension on the suture 10 to keep it in place in the catheter body 104. The second, proximal end suture loop 16 extends from the doubling point 14 distally until it is looped around a needle support tube 152 through which the needle is advanced to penetrate the leaflet and insert the suture around the leaflet.

Figure 5A:
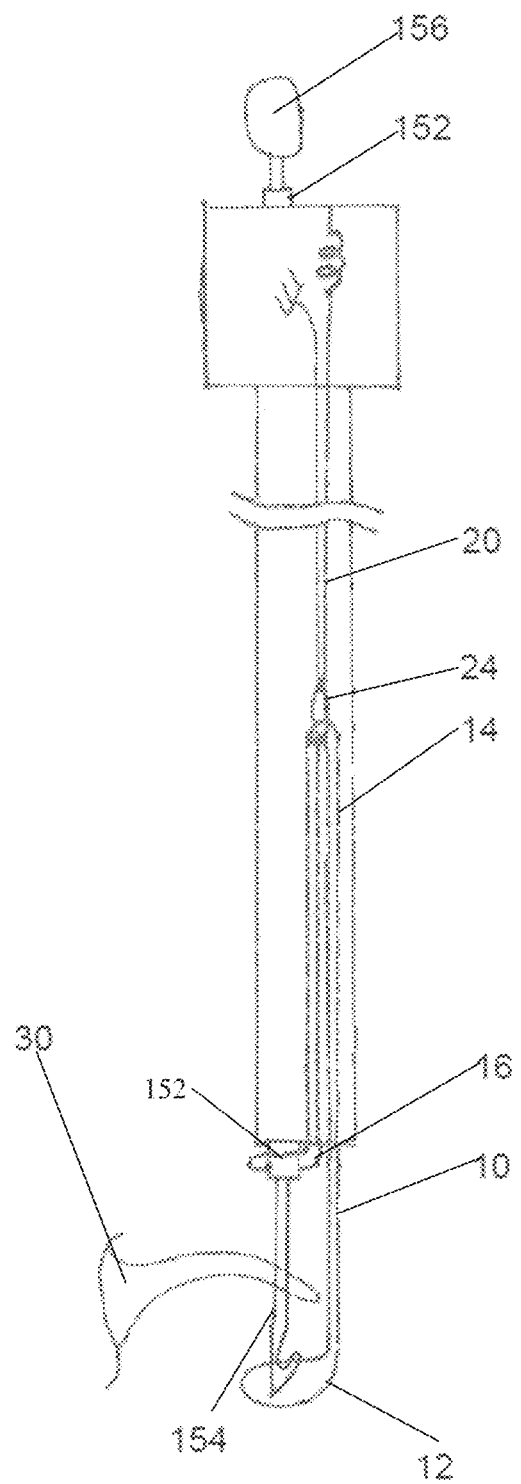
FIG. 5A-5D depict a sequence of steps for inserting one or more sutures into a valve leaflet according to an embodiment.

The proximal control mechanism 150 for the device 100, depicted schematically in FIG. 4B, consists of a main body that allows comfortable access to the controls of the device. The separate looped suture 20 is secured in the handle 150 by a spring 22 at one end of the loop 20, and a disengagable connection 24 at the other. As shown in FIG. 5A, the needle 154 extends through the control mechanism 150 and the proximal end of the needle contains a handle 156 which allows for comfortable access and control of the needle 154. The control handle also houses two sliding controls (not depicted). The first sliding control is connected to the distal jaw actuator such as flexible member 144 extending through a lumen in the catheter body 104. Distal relative movement of the first slider with respect to the control handle 150 will actuate the distal jaw 108. The second sliding control is connected by a flexible rod 148 extending through the catheter body 104 to the proximal jaw 108. Distal relative movement of the second slider with respect to the control handle 150 will actuate the proximal jaw 108. Further details regarding proximal controls for control elements at a distal end of a leaflet capture catheter can be found in U.S. Provisional Patent Application No. 62/647,162, filed Mar. 23, 2018, which is hereby incorporated by reference herein.

In some embodiments, one or more channels through the device could alternatively accommodate or could additionally be added to incorporate fiber optic capture confirmation elements. In such an embodiment, one or more pairs of transmission and return fibers run through the device to enable the capture confirmation system to provide a binary indication of whether the valve leaflet is grasped between the clamping jaws by displaying a first color when a surface of the valve leaflet confronts the fiber optic pairs and a second color (e.g., of blood) when the valve leaflet does not confront the fiber optic pairs at the interior surfaces. Further detail regarding fiber optic capture confirmation of a valve leaflet in a beating heart of a patient can be found in U.S. Pat. Nos. 8,465,500 and 8,758,393 and U.S. patent application Ser. No. 16/363,701, previously incorporated herein by reference.

Figure 5B:
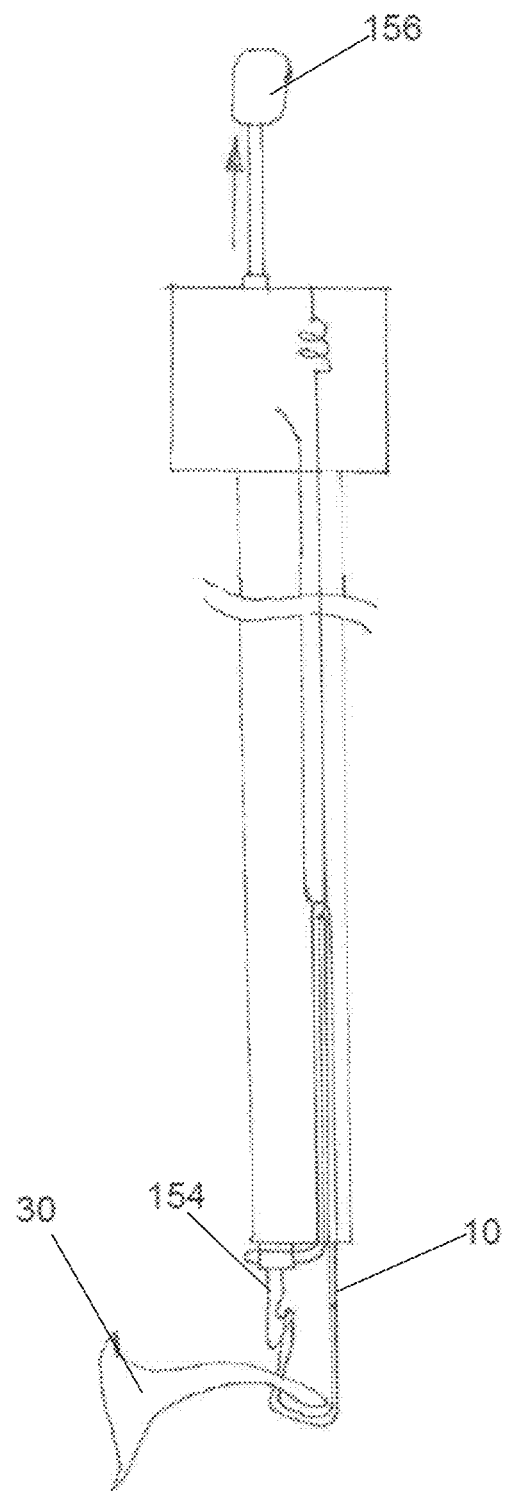
Figure 5C:
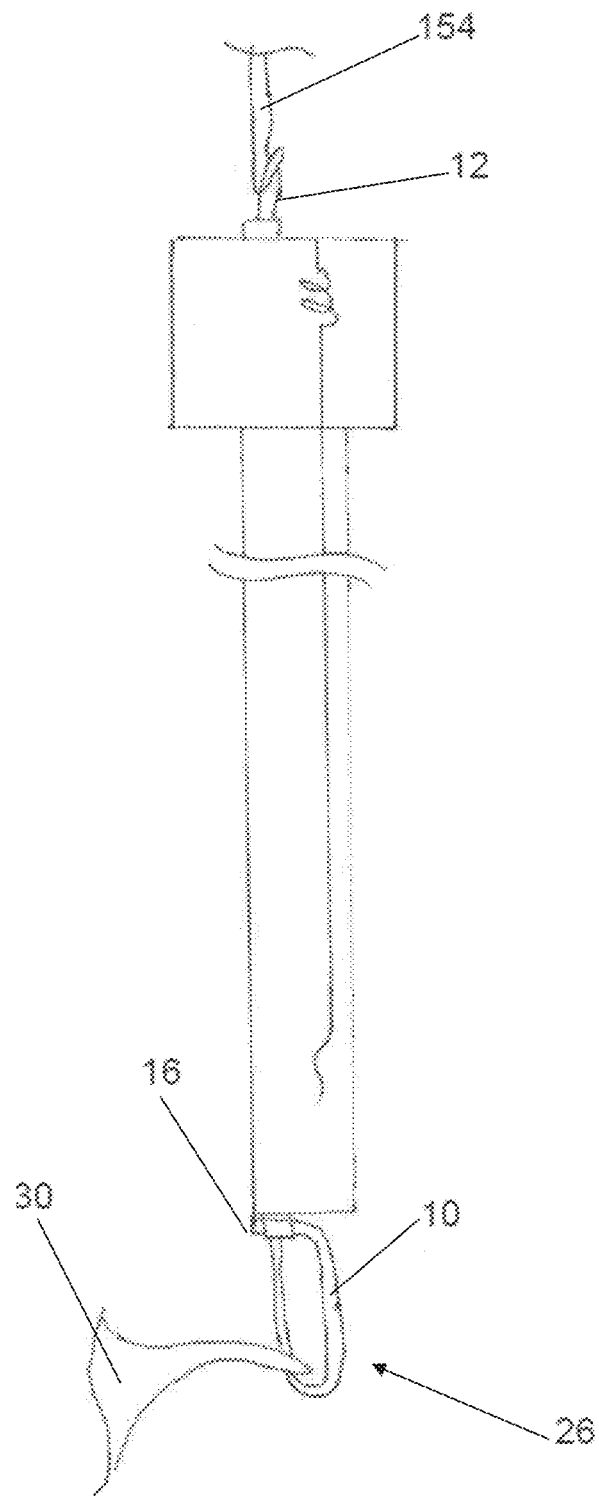
Figure 5D:
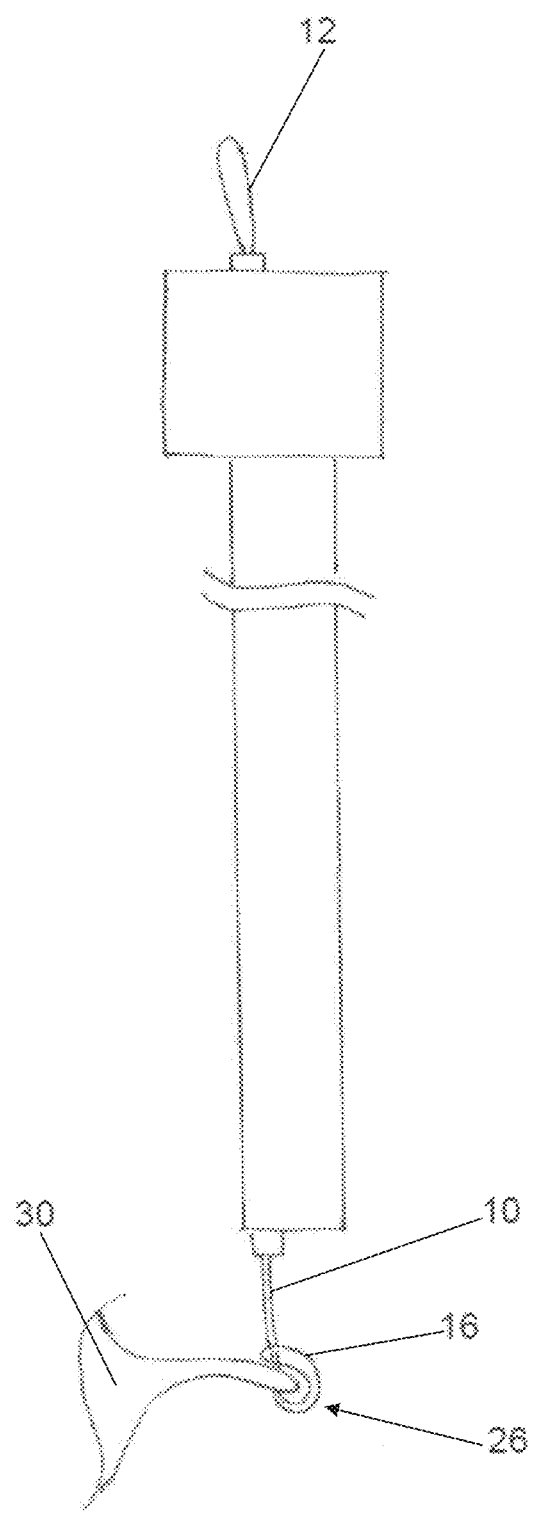
Figure 6:
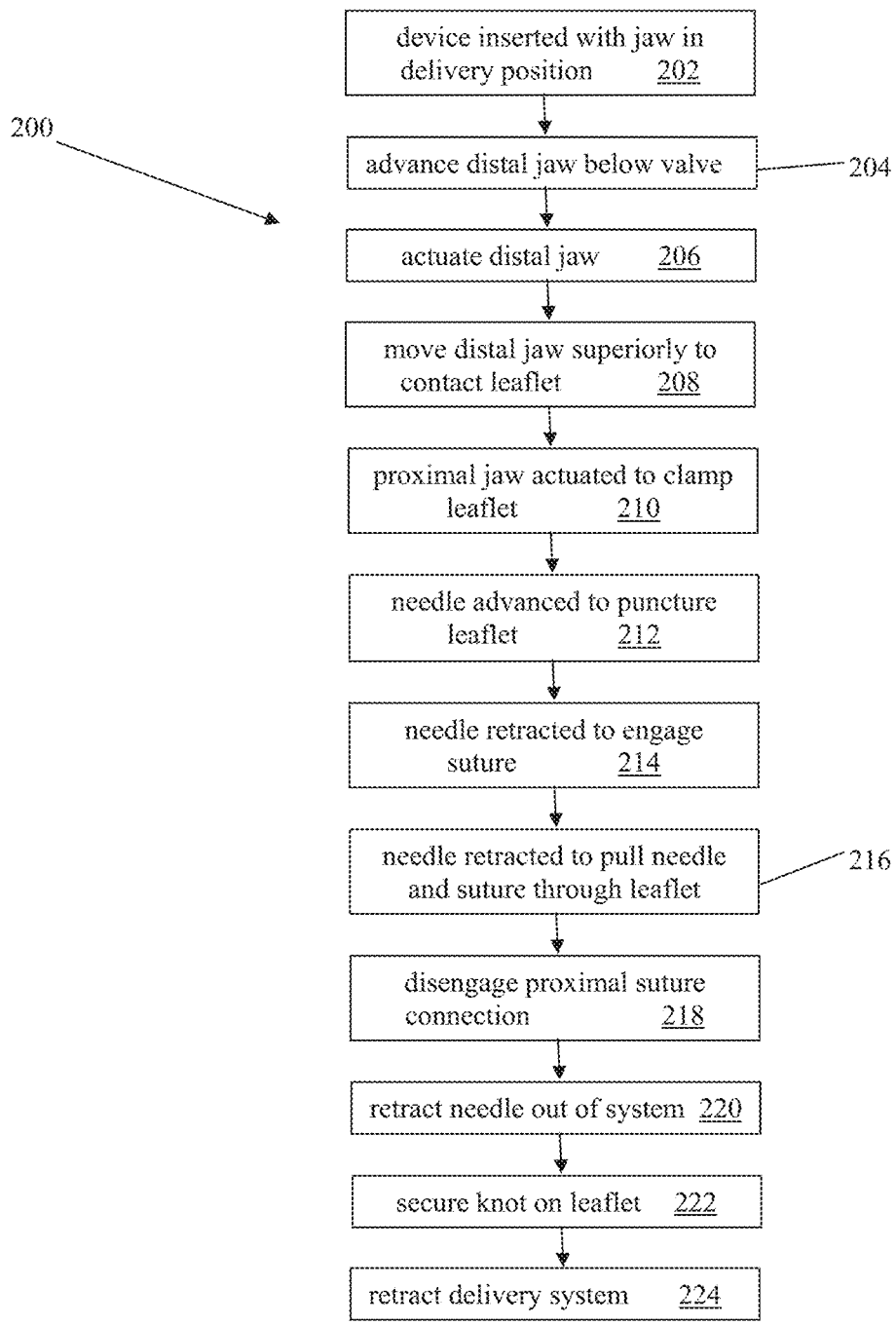
FIG. 6 depicts a flowchart of method steps for inserting one or more sutures into a valve leaflet according to an embodiment.

FIGS. 5A-5D depict a sequence of steps of an embodiment of using device 100 to insert one or more sutures into a valve leaflet and FIG. 6 depicts a flowchart of method steps 200 corresponding to the sequence. FIGS. 5A-5D depict the device 100 without the distal jaw 106 and proximal jaw 108 for sake of clarity. In step 202, the device is inserted through the delivery system with the distal jaw in the un-actuated, first delivery configuration. In embodiments, access into the heart adjacent the mitral valve can be gained intravascularly as described herein. Further details regarding such access can be found in U.S. Provisional Patent Application No. 62/647,162 incorporated by reference above. In embodiments, the device is inserted with two sutures 10 loaded into the device, though only a single suture 10 is depicted in FIGS. 5A-5D for sake of clarity.

After exiting the delivery system, the distal jaw of the device is advanced below the level of the mitral valve at step 204 and the distal jaw is actuated at step 206 moving the jaw to an angle in which it will contact the valve leaflet. After the device is positioned to the desired point of leaflet attachment, the system is moved superiorly at step 208 with respect to the valve until the lower (distal) jaw contacts the inferior side of the valve leaflet. The proximal jaw is then actuated at step 210 by sliding it along the rail until the leaflet is clamped and stabilized between the jaws.

Once the leaflet 30 is stabilized between the jaws, the needle 154 is advanced at step 212 puncturing the valve leaflet and extended through an opening in the distal jaw and between the suture segments that are positioned around the post and intermediate tabs in the distal jaw. The needle 154 is then retracted which engages the suture with the hook in the needle profile as shown in FIG. 5A at step 214. This pulls the distal suture loop 12 off from the distal post of the distal jaw and the needle can then pull the suture loop through the puncture in the valve leaflet 30 at step 216 as depicted in FIG. 5B. Due to the angle geometry of the intermediate tabs 126, a distal portion of the suture will remain wrapped around them keeping this distal portion of the suture from contacting the distal side of the leaflet. This enables the suture to be tightened without putting force on the leaflet that could potentially damage the leaflet. With the needle 154 on the proximal side of the valve leaflet 30 and the distal suture loop 12 in the needle hook, the disengagable connection 24 to the proximal suture loop 16 via the separate suture 20 looped around the double loop 14 is released in the control handle at step 218. Further retraction of the needle 154 at step 220 will then pull the proximal loop 16 distally into the system. At the point that the needle 154 is fully pulled from the system with the distal suture loop 12 that is in the needle 154 exposed, the resulting girth hitch knot 26 is very close to being tightened at the distal end of the system as depicted in FIG. 5C. The final step 222 to tighten the knot 26 is when the secured distal loop 12 is pulled distally from the needle tube allowing the knot 26 to be secured at the leaflet as depicted in FIG. 5D.

Once the knot 26 is tightened on the leaflet 30, the delivery system can be retracted at step 224. To do so, the proximal jaw may be released and moved proximally, unclamping the valve leaflet. The distal jaw is then un-actuated. The change in the distal jaw angle releases the suture from intermediate tabs 126 in the distal jaw which then fully detaches the system from the leaflet. The catheter can then be retracted into the delivery system or the optional second suture may be delivered by moving the system to a different position along the leaflet and repeating the process sequence described above.

Once one or more sutures have been attached to the leaflet, the suture(s) can be adjusted to provide an appropriate length and/or tension for proper valve function and anchored. Further details regarding tensioning and anchoring of sutures can be found in U.S. patent application Ser. Nos. 16/406,736; 16/406,764; and 16/406,799, each of which is hereby incorporated by reference herein.

Figure 7:
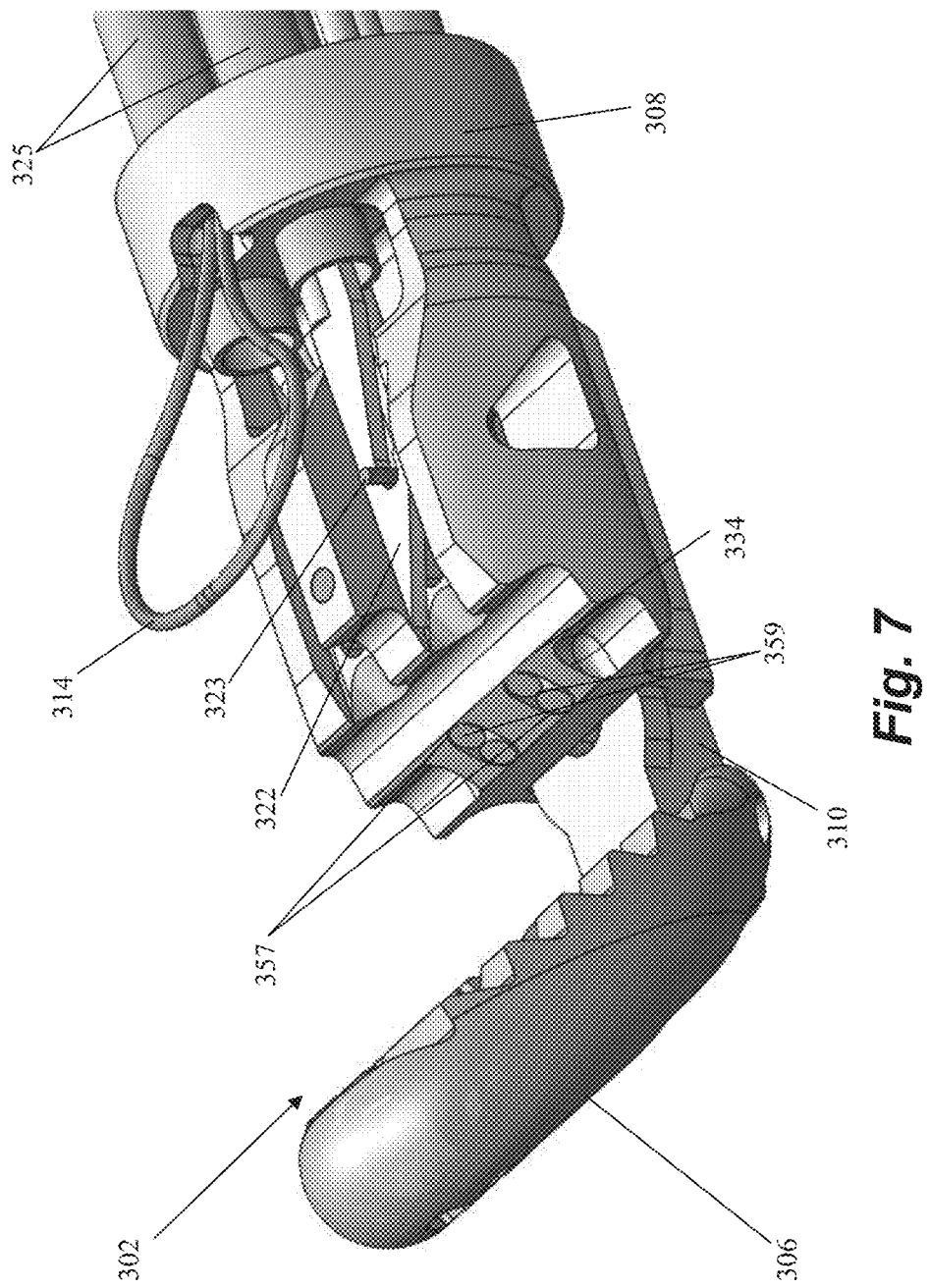
FIG. 7 depicts a distal end of a suture attachment device according to an embodiment.

FIG. 7 depicts another distal end of a leaflet capture catheter 302 according to an embodiment. In this embodiment, the proximal jaw 308 is stationary and longitudinally fixed in place. Rail 310 can be slidable to adjust the distance between proximal jaw 308 and distal jaw 306 to aid in leaflet capture as will be discussed in more detail below with regard to FIGS. 8A-8D. As with leaflet capture catheter 102, the distal jaw 306 can be pivotable to also aid in leaflet capture. Each needle 322 can include a keying wire 323 that retains the needle in place distally of the needle lumens 325. In one embodiment, keying wire 323 can be provided with a forward bias and the needle 322 a backward bias to keep the needle in place and when the needle 322 is pushed forward the wire 323 drops out of the path of the needle 322. In another embodiment, the keying wire 323 can be retracted, such as with a control element on the proximal handle of the device attached to the wire, such that no spring biases are utilized. This embodiment depicts two sets of fiber optic cables 359 (each including one transmission fiber and one return fiber) disposed in fiber optic channels at the distal clamping face 334 of the proximal jaw 108 to aid in verifying proper leaflet capture. The depicted embodiment further includes a stabilizing loop 314 as described in more detail below. Leaflet capture catheter 302 can further include any feature described with respect to the other embodiments disclosed herein.

Figure 8A:
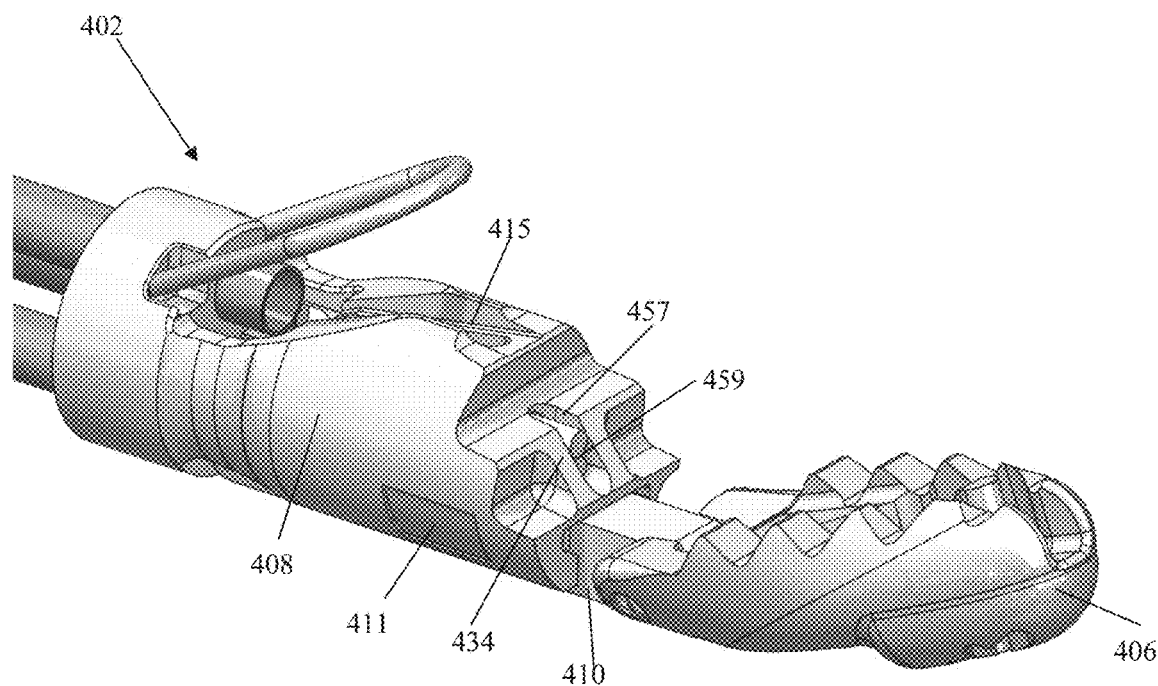
FIGS. 8A-8D depict a distal end of a suture attachment device according to an embodiment.
Figure 8B:
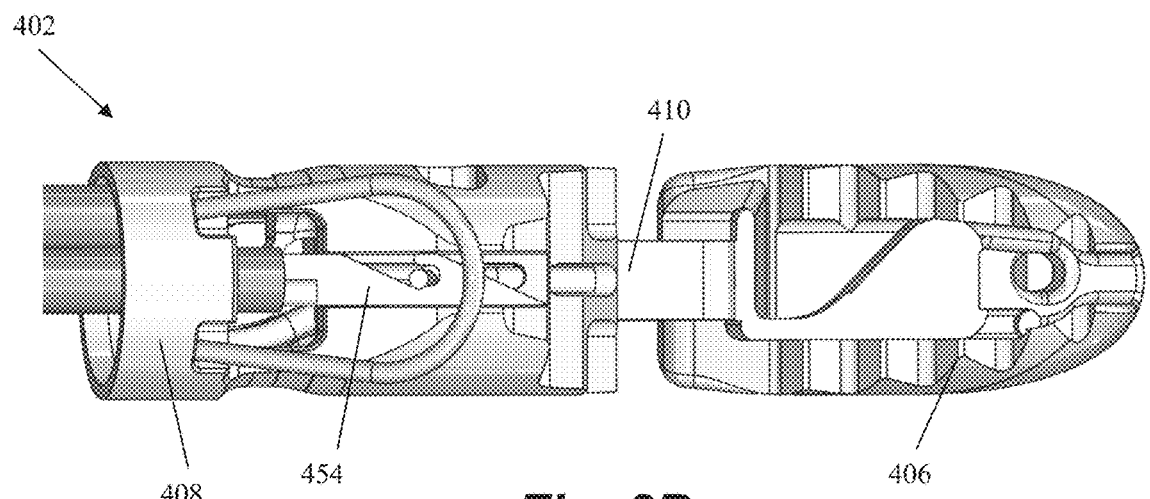
Figure 8C:
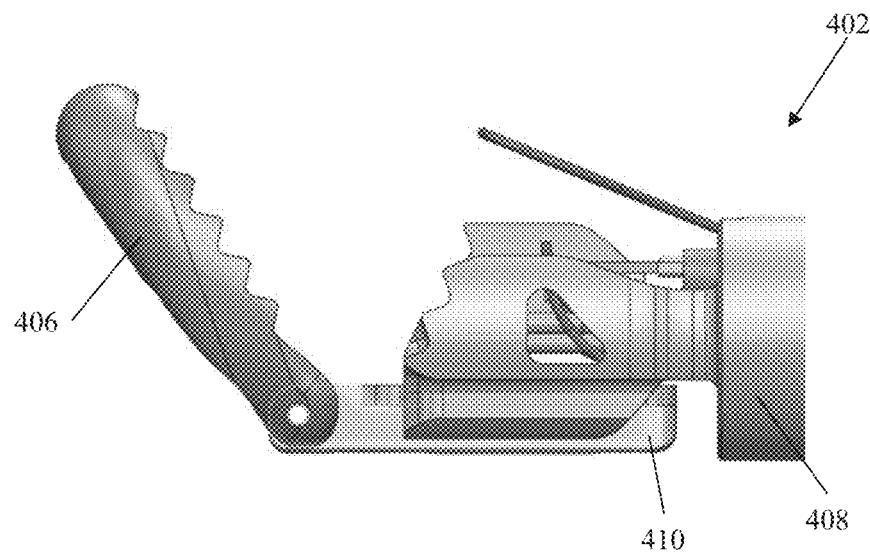
Figure 8D:
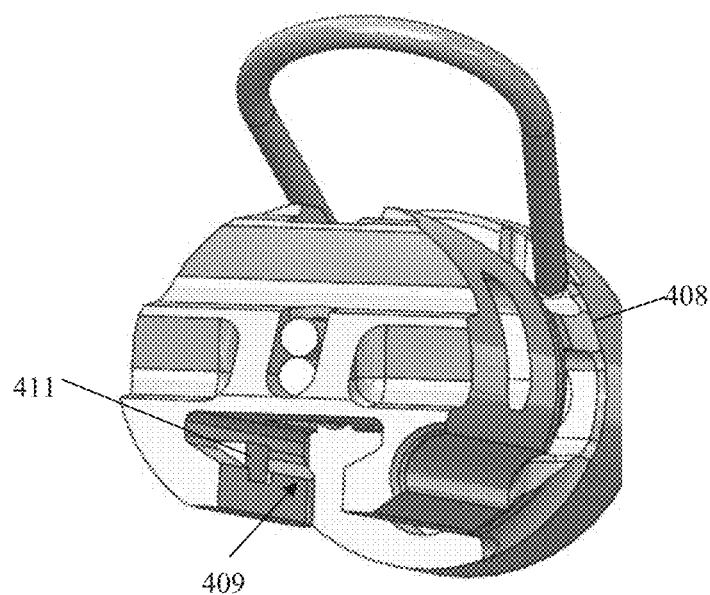

FIGS. 8A-8D depict another distal end of a leaflet capture catheter 402 according to an embodiment. This embodiment can be configured to carry only a single suture and a single needle 454 and can have a single pair of fiber optics 459 in a fiber optic channel 457. Distal jaw 406 can be hingedly attached to rail 410. Rail 410 can be slideable with respect to proximal jaw 408 to adjust a separation distance between the jaws 408, 410. Referring to FIGS. 8C-8D, rail 410 can have limited length and be connected to a hypotube (not pictured) controllable from the proximal handle to slide rail 410 within a rail channel 409 defined in proximal clamping jaw 408. Proximal jaw 408 can further including a locking tab 411 that can mechanically interact with a locking feature on rail 410 to prevent the rail 410 from being completed moved distally from the rail channel 409. In embodiments, the rail 410 can be biased proximally, towards a closed position with a spring force that is overcome to open the jaws, which enables the jaws to remain clamped around a leaflet once a leaflet is captured. Referring to FIG. 8A, the needle channel 415 along proximal jaw 408 across which the needle 454 travels to engage the leaflet can be ramped at an upwards angle to ensure the leaflet is pierced sufficiently above the leaflet edge. Leaflet capture catheter 402 can further include any feature described with respect to the other embodiments disclosed herein.

Figure 9A:
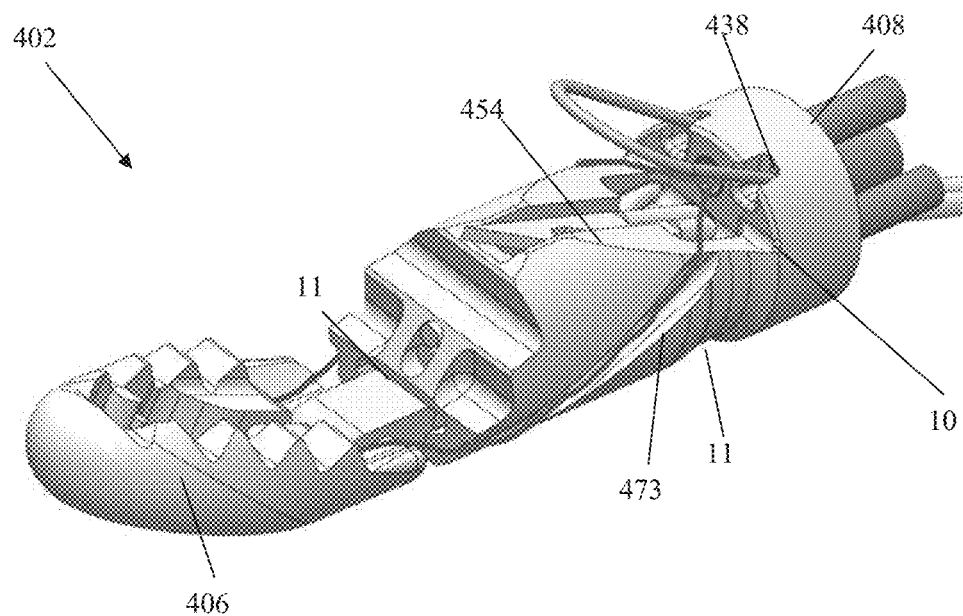
FIGS. 9A-9B depict a distal end of a suture attachment device according to an embodiment.
Figure 9B:
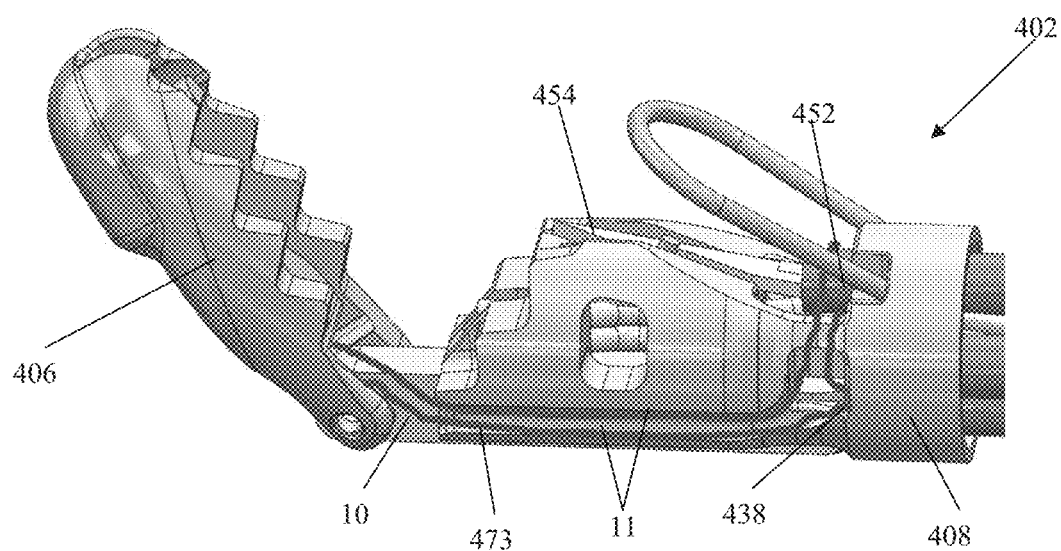

FIGS. 9A and 9B depict alternatives as to how a suture can be routed to the distal capture jaw of any of the leaflet capture catheters disclosed herein including, for exemplary purposes, leaflet capture catheter 402. Referring to FIG. 9A, in this embodiment the suture 10 extends from a lumen 438 in the proximal clamping jaw 408, with each strand 11 of the suture extending around a channel 473 one either side of the proximal clamping jaw 408. The strands then extend up and form a loop at the distal clamping jaw for retrieval by the needle 454. The suture 10 extends back to the proximal handle control where it can be maintained under an appropriate tension for retrieval by the needle. In this embodiment, the suture lumen 438 is positioned above the needle 454 such that the suture 10 emerges from the proximal clamping jaw 408 from above the needle 454. Referring now to FIG. 9B, in this embodiment the suture 10 extends from a lumen 438 in a lower part of the proximal clamping jaw 408 below the needle 454 and wraps around the needle tube 452 containing the needle 454. Both suture ends 11 then extend along the same channel 473 on a single side of the proximal clamping jaw 408 and to the distal clamping jaw 406. The suture 10 also can then extend back to the proximal handle control. For suture capture by the needle 454, the suture 10 is released from the needle tube 452 by an actuation means, such as a control mechanism that attaches to and withdraws the tube or a wire that holds the suture on the tube and is then retracted, for example. In each of these embodiments, the suture 10 can be held in the proximal jaw by a variety of means including, for example, with features such as the distal posts 122 and intermediate tabs 126 described above.

Both of the embodiments of FIGS. 9A-9B greatly simply the suture routing and tensioning aspects of the device with respect to, for example, FIG. 4B. The suture 10 in these embodiments is no longer folded in half and can extend back to the handle, eliminating the need for the separate looped suture 20 and disengageable connection 24 as well as, in the embodiment of FIG. 9A, the proximal end suture loop 16 around the needle tube 152.

FIGS. 10A-10D depict another distal end of a leaflet capture catheter 502 according to an embodiment. Leaflet capture catheter 502 is substantially similar to the leaflet capture catheter 402 described with regard to FIGS. 8A-8D, and any features of either leaflet capture catheter could be utilized with the other. Leaflet capture catheter 502 can further include any features described with respect to the other embodiments disclosed herein. As with previous embodiments, catheter 502 includes a proximal clamping jaw 508 and a distal clamping jaw 506 having an adjustable separation distance via rail 510.

Figure 10A:
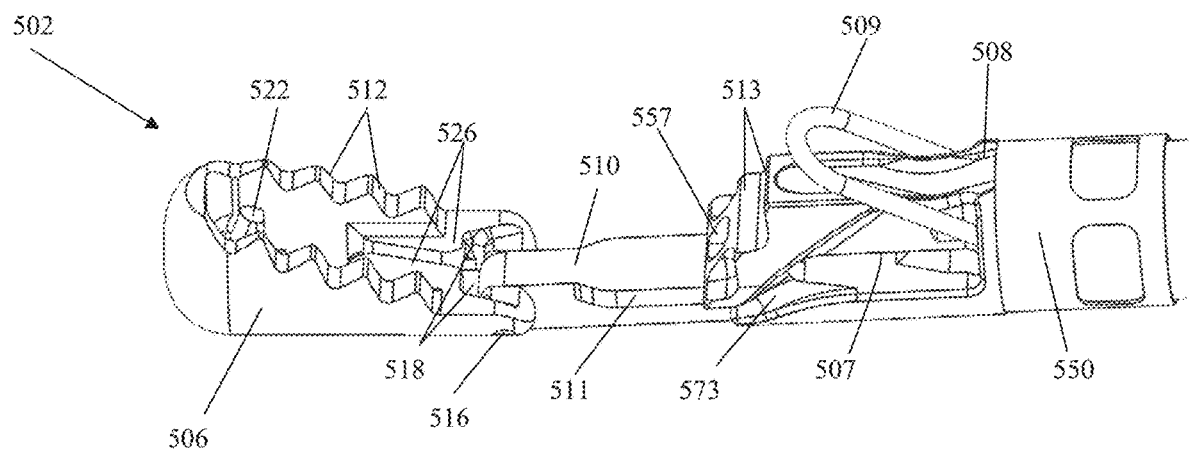
FIGS. 10A-10D depict a distal end of a suture attachment device according to an embodiment.
Figure 10B:
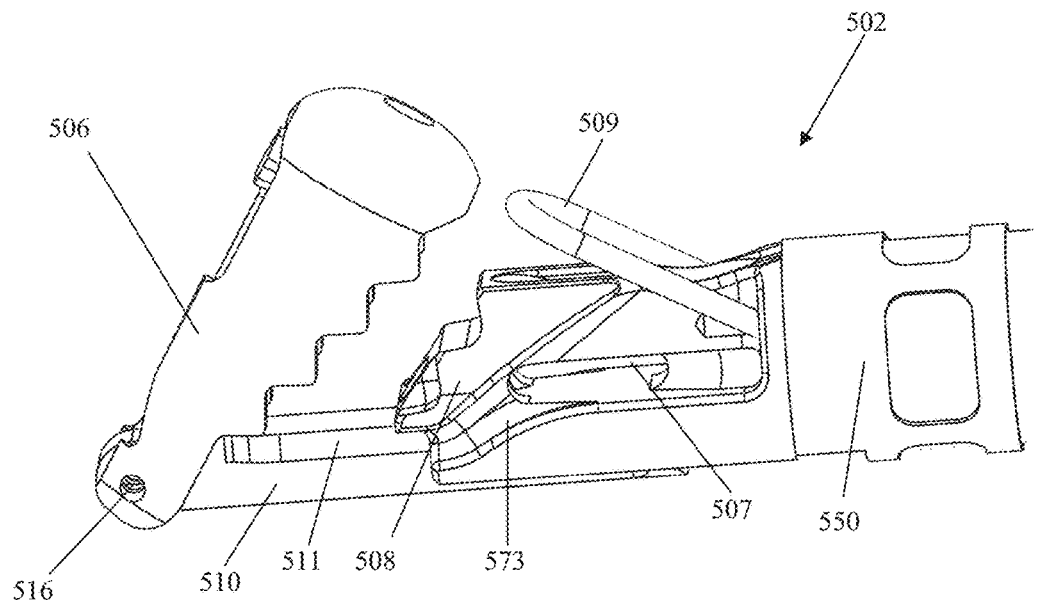
Figure 10C:
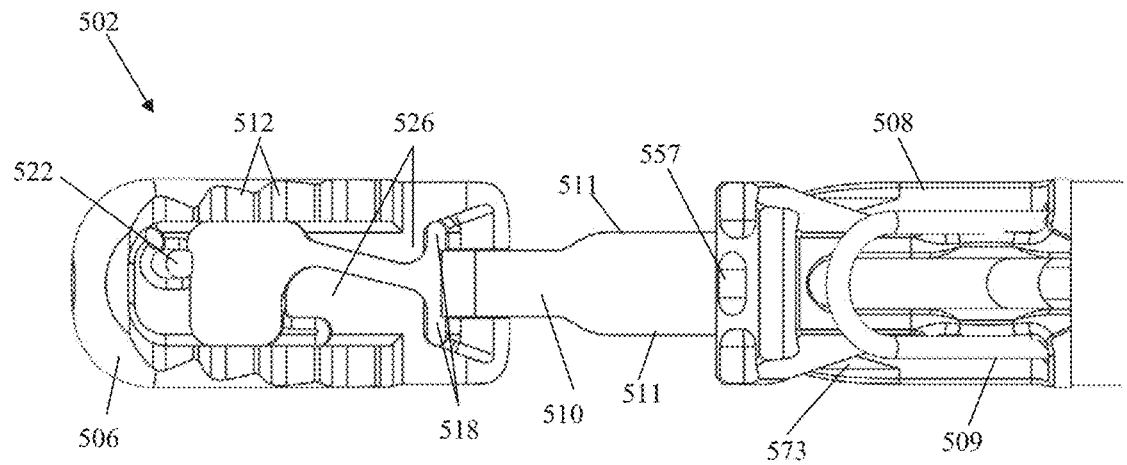
Figure 10D:
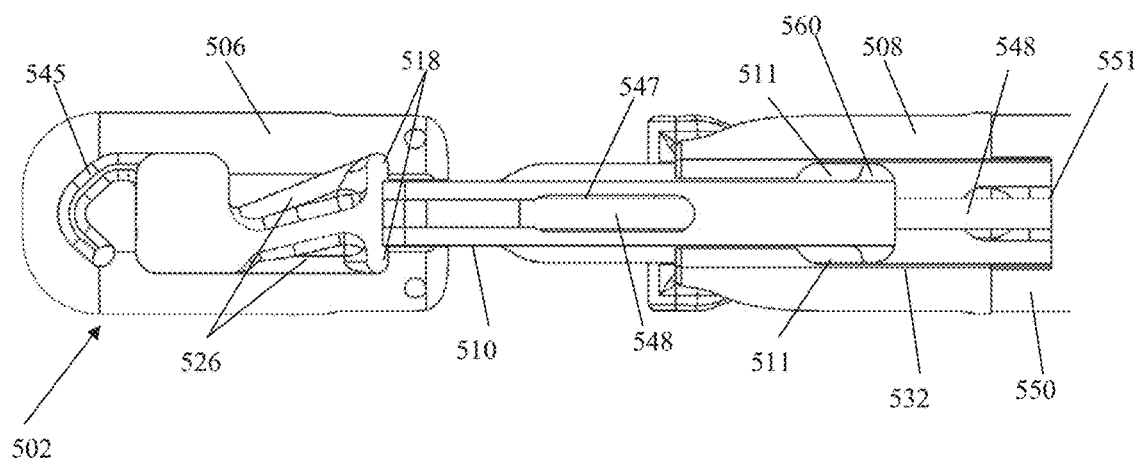
Figure 11A:
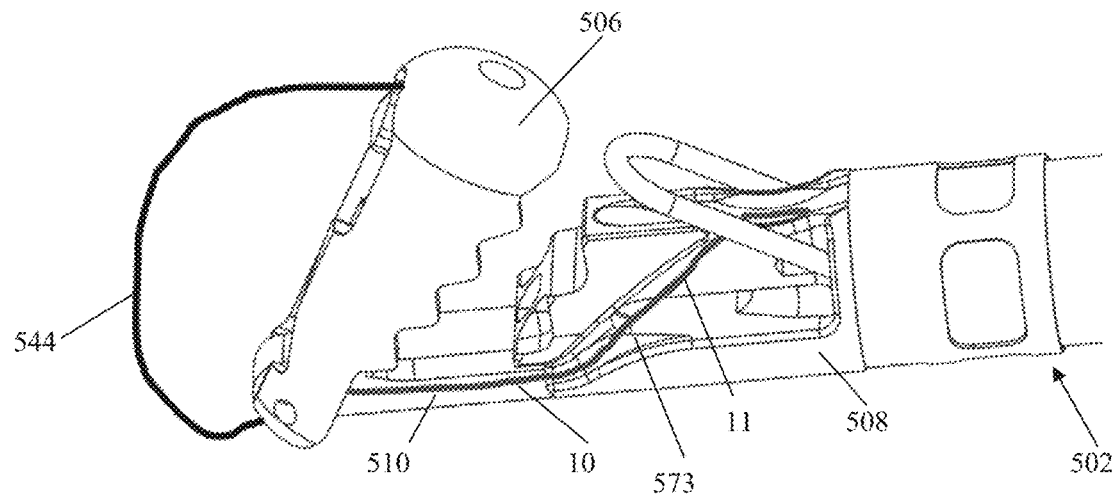
FIGS. 11A-11C depict a distal end of a suture attachment device according to an embodiment.
Figure 11B:
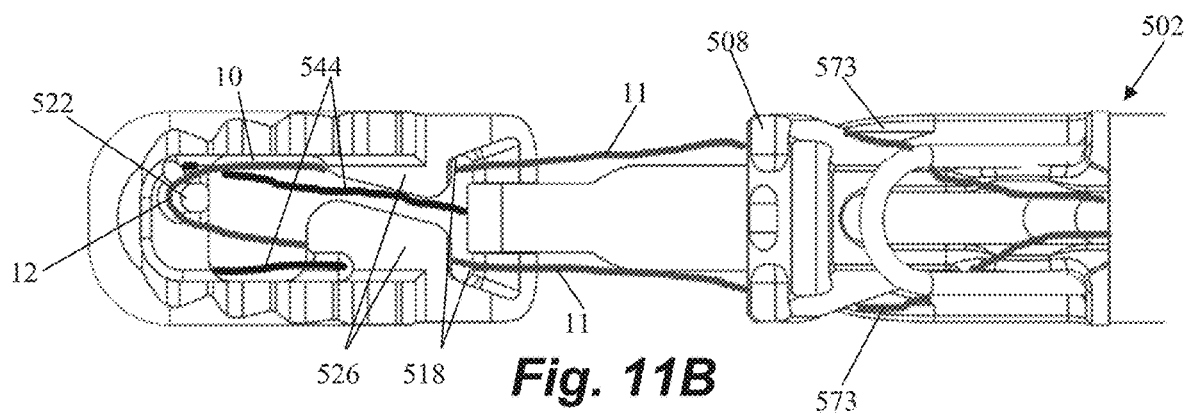
Figure 11C:
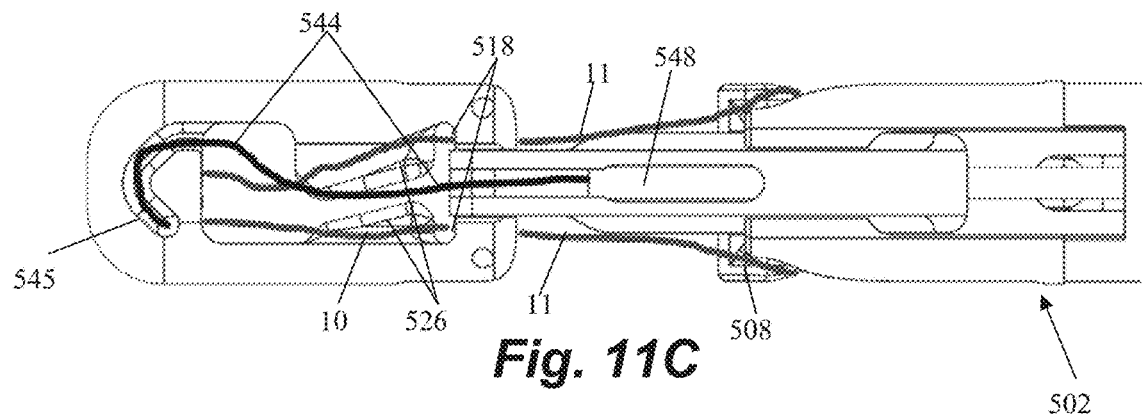

Distal jaw 506 can be hingedly attached to rail 510 with hinge pin 516 and can be actuated from the open, delivery position (depicted in FIG. 10A) to the closed, clamping position (depicted in FIG. 10B) with a flexible member 544 such as that depicted in FIGS. 11A-11C and described above with respect to catheter 102. For the closed position, the distal jaw 506 can be pivoted to an angle with respect to the rail that generally matches an angle of the proximal jaw 508 as depicted in FIG. 10B. Distal jaw 506 can include a wire housing 545 having a slot into which the flexible member 544 is inserted and configured to retain the flexible member 544 therein. As will be shown in more detail below, flexible member 544 is routed through the distal jaw 506 and into the wire retainer 545 in such a manner that it is retained in place without any glue or welding required. The distal jaw 506 can be configured to stop pivoting at the depicted capture angle due to the bottom of the jaw abutting the rail, which prevents the jaw from being pivoted too far. Distal jaw 506 can further include suture retention features, including suture routing post 522, distal suture routing fins 526 and suture routing lumens 518, which will also be discussed in more detail below. Leaflet grasping teeth 512 can be disposed around a perimeter of distal jaw 506 to aid in retaining a clasped leaflet.

Proximal jaw 508 can similarly include ridged or stepped surfaces 513 that function as leaflet grasping teeth to aid in retaining a leaflet between jaws 506, 508. An optics housing 557 can be disposed in proximal jaw 508 to contain fiber optics for confirming leaflet capture. Proximal suture routing fins 573 can be disposed on both sides of proximal jaw 508 to aid in guiding and retaining suture, as described in more detail below. As with previous embodiments, a wire loop 509 can be provided to aid in suture capture and retention by pivoting upwards after the leaflet capture catheter 502 exits the delivery catheter to increase the surface area of the proximal jaw 508 for leaflet capture. The expanded configuration is depicted in FIGS. 10A-10B, in which the wire loop has pivoted up above the proximal jaw. Proximal jaw 508 can be provided with loop cutouts 507 along the sides of jaw to allow the wire loop 509 to be retained along the sides of catheter 502 when in the compressed configuration without increasing the French size of the device.

Rail 510 is slidably extendable from a slot 532 in proximal jaw 508 to adjust the distance of distal jaw 506 from proximal jaw 508. A rail slide hypotube 548 that extends back to a device handle can be inserted into a slide lumen 547 in rail and fixed to rail by, e.g., soldering, to enable control of movement of rail 510 and distal jaw 506 from the handle. As will be discussed in more detail below, flexible member 144 can extend through slide hypotube 548 between the handle and the wire housing 545 in the distal jaw 506 to enable pivoting control of the distal jaw 506 via flexible member 144 from the handle. Rail 510 can further include rail slide fins 511 that extend outwardly from a body of rail 510. Rail slide fins 511 extend the full with of the slot 532 to limit the rail 510 to longitudinal or axial movement. Fins 511 are provided with stop features or projections 560 on the proximal end of fins that prevent the rail 510 from being extended completely out of the distal end of the slot 532 of the proximal jaw 508.

Leaflet capture catheter 502 can further include a jaw attachment hypotube 550 disposed between the catheter body of the device and the proximal jaw component 508. Jaw attachment hypotube 550 can be a separate hypotube that is, e.g., laser cut, and then reflowed onto the catheter body and laser welded to the proximal jaw to connect the leaflet capture end of the device to the catheter body. Jaw attachment hypotube 550 can further include a proximal rail stop 551 that prevents the rail 510 from moving proximally to a position that would move the distal jaw 506 too close to the proximal jaw 508.

Referring now to FIGS. 11A-11C, leaflet capture catheter 502 is schematically depicted with a flexible member 544 and a suture 10 routed therethrough. Flexible member 544 extends through and out of rail slide hypotube 548 in rail 510 and then extends around distal jaw 506 and into wire housing 545. Suture 10 can be configured as a closed loop having a pair of suture ends that extend out of a common opening in the face of proximal jaw 508, along proximal suture routing fins 573, underneath the distal portion of proximal jaw 508 and then along each side of the rail 510 towards the distal jaw 506. Each suture end 11 then extends through one of the suture routing lumens 518 in the distal jaw 506, beneath one of the suture routing fins 526, and one end of the suture loop 12 is wrapped around suture routing post 522 under tension for retrieval by needle. Suture routing lumens 518 keep the suture mounted on the distal jaw while the needle is retrieving the suture. When the needle grasps the suture, it pulls the suture off of the suture routing post 522 and back through the leaflet. Suture routing fins 526 keep the suture fixed in the jaw until the suture is completely retrieved by the needle. Once the suture is retrieved, the distal jaw is opened, which releases both the leaflet and the suture from the distal jaw. The suture loop can be formed by tying a knot with the two suture ends. In embodiments, a blood knot can be tied, reinforced with adhesive, and then crimped to reduce the profile. Further details for suture routing and tensioning (generally in the context of a transapical procedure) can be found in U.S. Pat. No. 8,758, 393 and https://neochord.com/wpcontent/uploads/2019/02/700010-002_Rev_5_IFU_pc_eng.pdf.

FIGS. 12A-12F depict a handle 600 for controlling a leaflet capture catheter, such as, for example, leaflet capture catheter 502, according to an embodiment. Although handle 600 will be specifically described for exemplary purposes with regard to control of leaflet capture catheter 502 depicted in FIGS. 10A-10D and 11A-11C, it should be understood that handle 600 could be utilized and/or adapted for use with other leaflet capture catheters, including the other leaflet capture catheters described and depicted herein.

Handle 600 includes a handle body 602 that houses and/or connects to a number of components for controlling leaflet capture catheter and performing a mitral valve repair procedure. A hemostatis hub 604 can be disposed within housing. Hemostatis hub can be a valved structure that prevents blood from leaking back from the catheter into the handle and can also enable air to be flushed from the system through a flush port 606 that connects to hemostasis hub 604 through housing 602 via tubing 608. Flush port 606 can further enable the device to be flushed with saline to clean out the catheter. A strain relief knob 610 comprised of a flexible material can be disposed at a distal end of handle 600 with catheter body extending therethrough to aid in preventing the catheter body from kinking during the procedure. A suture tensioning assembly 612 can also be disposed within housing 602 to maintain the suture under the tension that keeps the suture positioned at the distal end of the device as described above until captured by the needle. In an embodiment, suture tensioning assembly 612 can include a tensioned spring 613 with an attached o-ring 615 to releasably hold the suture under tension.

Handle 600 further includes a number of control elements that enable an operator to control elements at the distal end of leaflet capture catheter 502 from the proximal portion of the device externally of the body. A rail slide actuation member 614 can be disposed in the housing and connected to the rail slide hypotube 548 such that forward movement of the rail slide actuation member 614 causes the rail slide 510 and distal jaw 506 to move forward and increase a distance between the distal jaw 506 and the proximal jaw 508. In embodiments, a spring or other resilient element (not pictured) contained in housing can bias the rail slide actuation member 614 and distal jaw 506 to the proximal, closed position. A flexible member actuation nut 616 can be disposed in the housing 602 and affixed to the flexible member 544 such that rotation (e.g., clockwise) of the actuation nut 616 moves the flexible member 544 forward to pivot the distal jaw 506 to the closed position. Reverse rotational movement of the actuation nut 616 (e.g., counter-clockwise) can therefore pull the flexible member 544 back to pivot the distal jaw 506 back to the open position. A control knob 618 can extend distally of the housing 602 for control of both the rail slide actuation member 614 and the flexible member actuation nut 616. Control knob 618 can be functionally linked to rail slide actuation member 614 and flexible member actuation nut 616 such that pushing or pulling control knob 618 moves the rail slide actuation member 614 (and distal jaw 506) distally and proximally and rotation of control knob 618 moves the flexible member 544 (thereby opening or closing the distal jaw 506) such that both functions can be controlled with a single control element. Control knob 618 can include a threaded portion 617 along which actuation nut 616 can travel when control knob 618 is rotated. A slot 619 can be disposed on housing in order to provide an operator with visual confirmation that the distal jaw is opened or closed based on the position of actuation nut 616.

Handle 600 can further be used to control the needle for puncturing the leaflet and retrieving the suture back through the leaflet. A needle release assembly 620 can include a needle grip 622 and a release handle 624 biased apart by a resilient element such as a spring 626. Needle release assembly 620 can be functionally connected to the needle such that the needle is prevented from moving forward out of the proximal jaw 608 until the user compresses the needle grip 622 and release handle 624 to overcome the bias of the spring 626. A needle window 623 can be provided through housing 602 to enable on operator to visually confirm needle deployment. A suture release pin 628 can be disposed within the housing 602 and controlled with a release lever 630 on the housing. Actuation of the release lever 630 removes the suture release pin 628 to free the suture for retrieval and enable remove of the needle handle assembly 620 to retrieve the needle with the suture. In embodiments, the release lever 630 rests on a ledge that prohibits the lever 630 from moving down to release the suture release pin 628 such that the lever must be slid horizontally in order to be moved down in order to prevent accidental release. A needle window 623 can be provided through housing 602 to enable on operator to visually confirm needle deployment prior to releasing the suture.

Figure 12A:
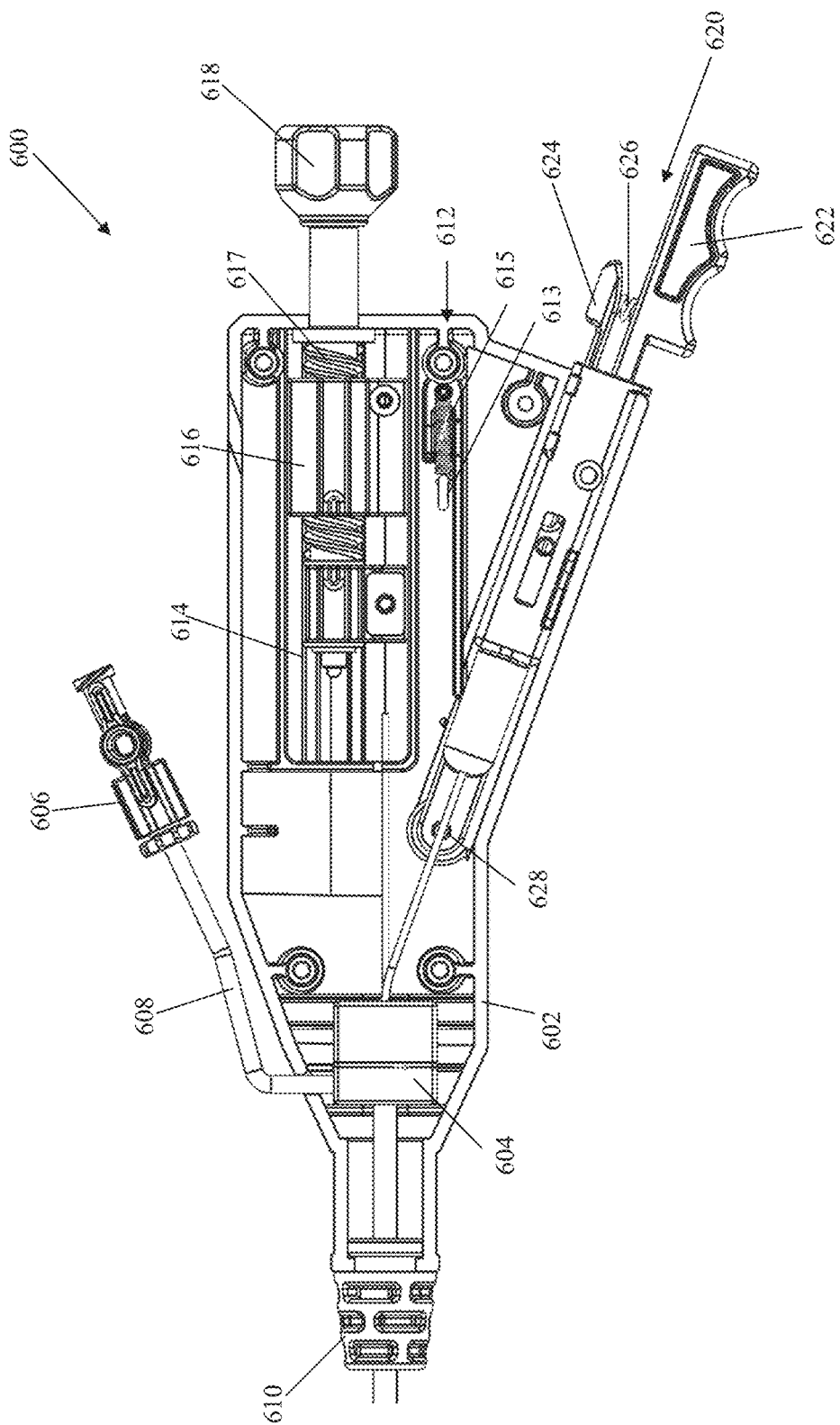
FIGS. 12A-12F depict a handle end of a suture attachment device according to an embodiment.
Figure 12B:
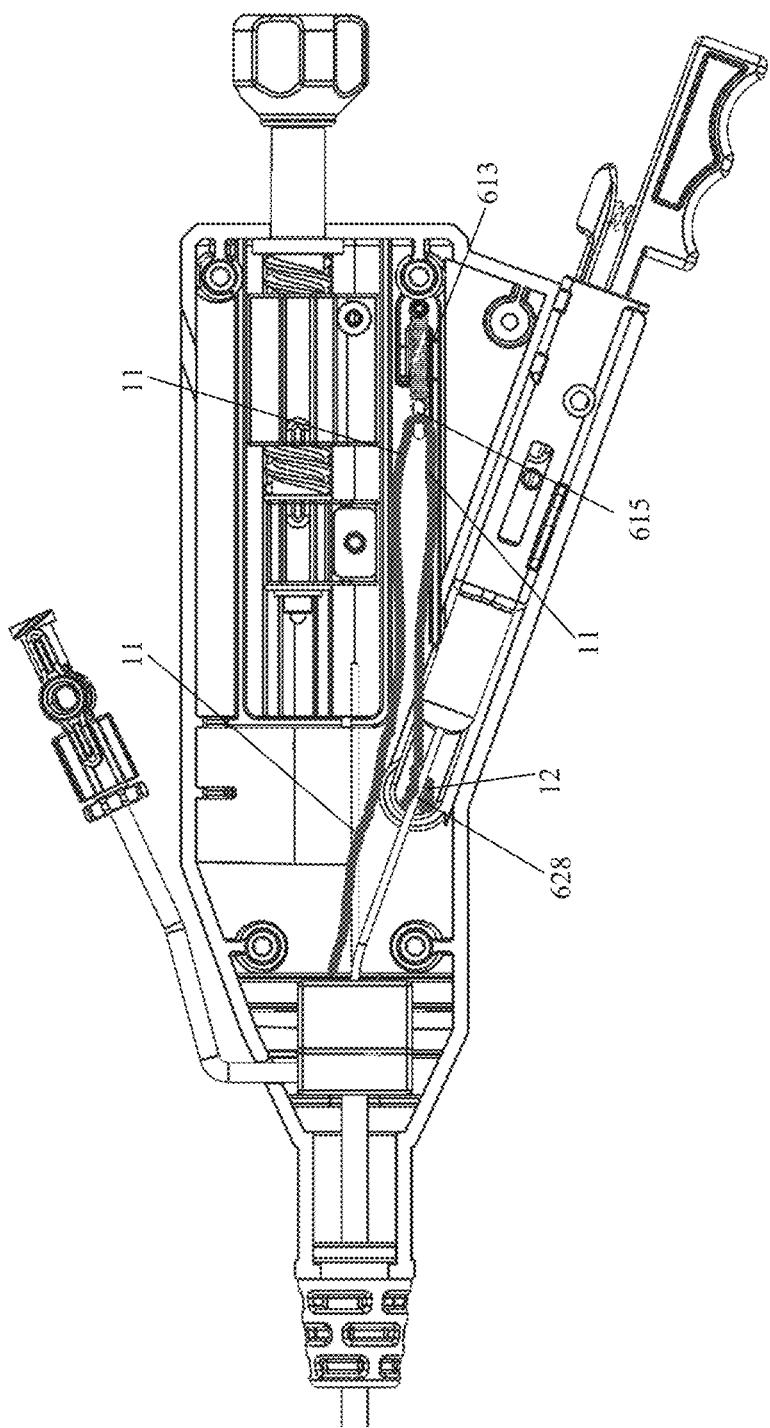
Figure 12C:
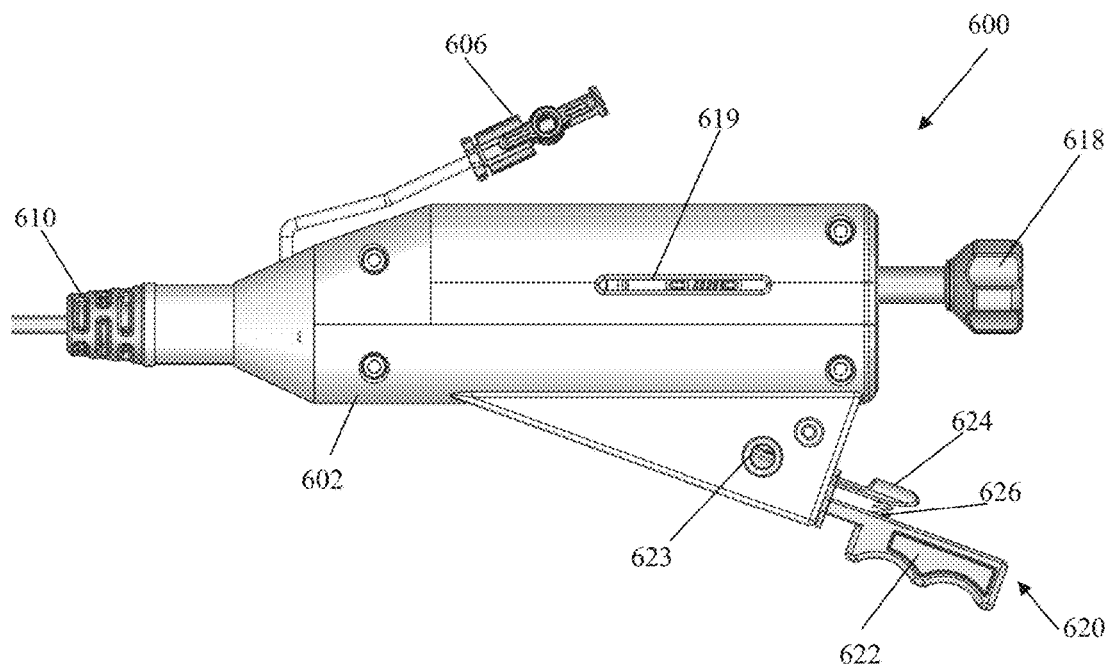
Figure 12D:
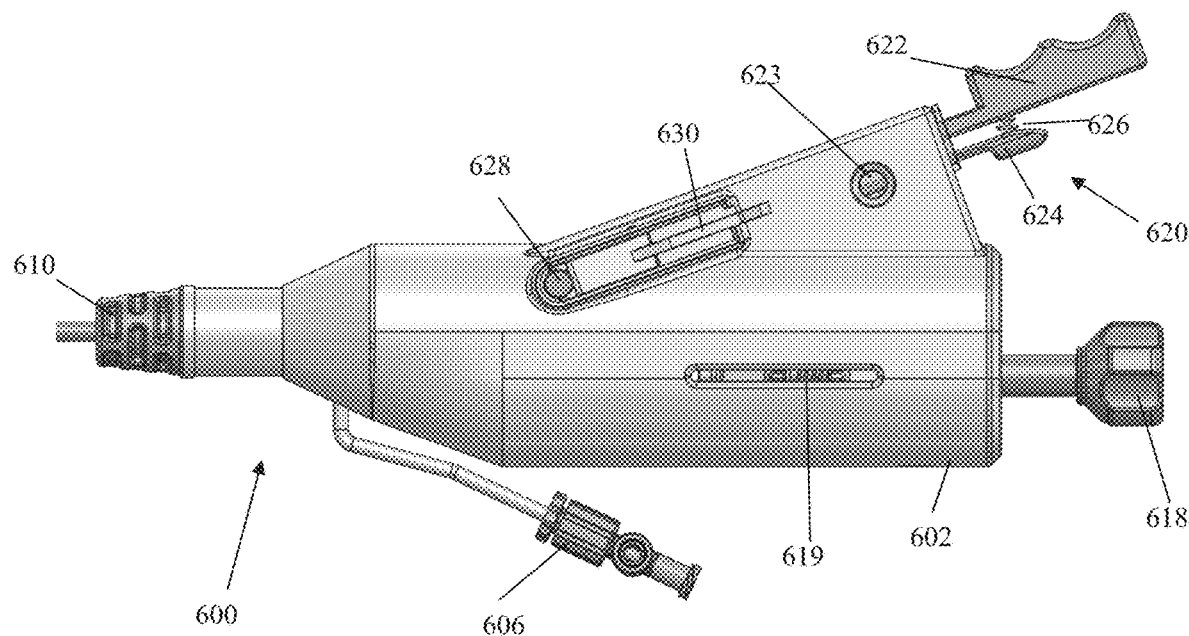
Figure 12E:
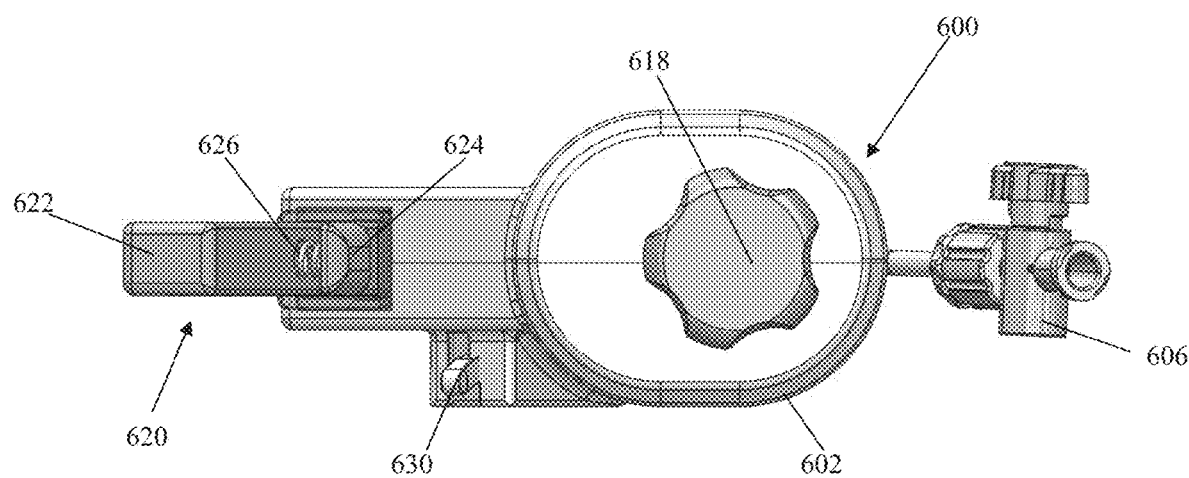
Figure 12F:
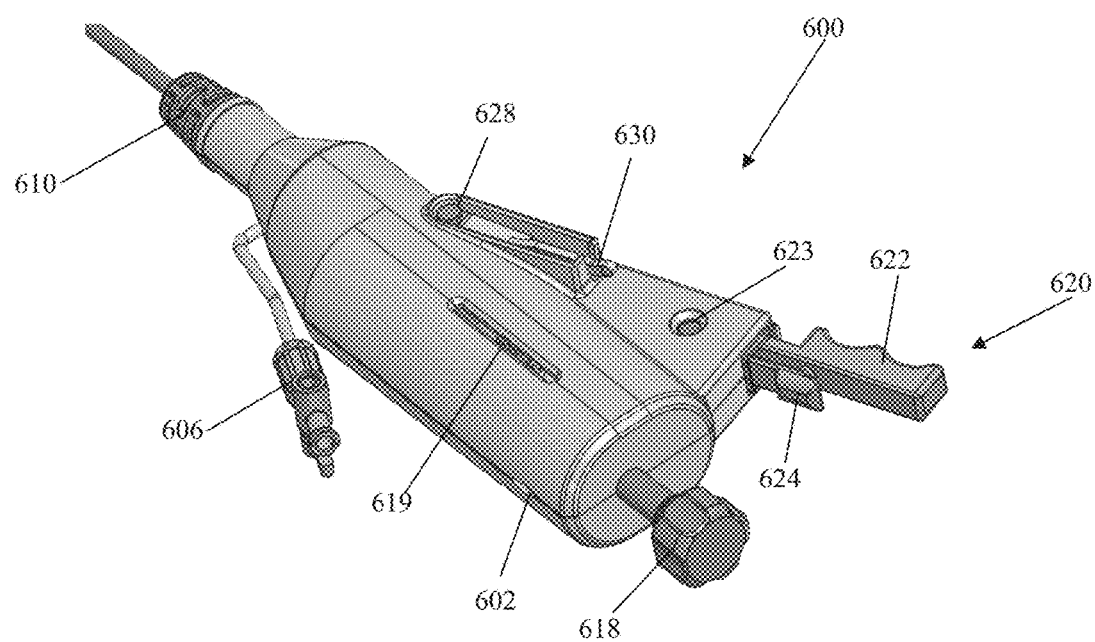

FIG. 12B depicts the routing of a suture 10 through the handle 600 according to an embodiment. The suture loop 12 exits through the hemostatis hub 604 and wraps around the o-ring 615 attached to the tensioning spring 613 of the suture tensioning assembly 612. The end of the suture loop 12 is placed over the suture release pin 628 to enable the suture to be retrieved from the distal jaw 506 upon actuation of the release button 620.

Although specifically described with respect to the mitral valve, it should be understood the devices described herein could be used to treat any other malfunctioning valve, such as the tricuspid and aortic valves. Further, although it should be understood that the devices described in the present application could be implanted into the beating heart of the patient via various access approaches known in the art, including transapical approaches (e.g., through the apex of the left ventricle) and transvascular approaches, such as transfemorally (through the femoral vein). One example of a transapical access approach that could be employed is described in U.S. Pat. No. 9,044,221, previously incorporated by reference herein. One example of a transvascular access approach that could be employed is described in U.S. Patent Publication No. 2013/0035757, which is hereby incorporated by reference herein. This versatility in access approach enables the access site for the procedure to be tailored to the needs of the patient.

Various embodiments of systems, devices, and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

For purposes of interpreting the claims, it is expressly intended that the provisions of 35 U.S.C. § 112(f) are not to be invoked unless the specific terms "means for" or "step for" are recited in a claim.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

The invention claimed is:

1. A suture attachment catheter configured to repair a heart valve by inserting a suture in a valve leaflet of a beating heart of a patient, comprising:
   a generally flexible catheter body having a proximal end, a distal end and a length greater than 100 cm;
   a suture attachment assembly proximate the distal end of the catheter body, the suture attachment assembly including:
      a proximal clamping jaw disposed adjacent the distal end of the catheter body;
      a rail having a proximal portion and distal portion, the proximal portion configured to be selectively longitudinally slideable with respect to the proximal clamping jaw; and
      a distal clamping jaw hingedly attached to the distal portion of the rail;
   a control handle operable attached to the proximal end of the catheter body, the control handle including:
      a rail actuator configured to selectively longitudinally slide the rail with respect to the proximal clamping jaw; and
      a jaw actuator configured to selectively pivot the distal clamping jaw between a first position for delivery of the suture attachment assembly into the heart and a second position for capturing a valve leaflet between the proximal clamping jaw and the distal clamping jaw; and
   a flexible member extending from the jaw actuator through the catheter body to a distal surface of the distal clamping jaw, wherein the jaw actuator selectively moves the flexible member to pivot the distal clamping jaw.

2. The suture attachment catheter of claim 1, further comprising a control knob at the control handle, wherein the control knob is configured to control both the rail actuator and the jaw actuator.

3. The suture attachment catheter of claim 2, wherein the control knob is configured to moved longitudinally to control the rail actuator and to be rotated to control the jaw actuator.

4. The suture attachment catheter of claim 1, wherein the flexible member extends into a housing in the distal clamping jaw.

5. The suture attachment catheter of claim 1, wherein the flexible member comprises a wire.

6. The suture attachment catheter of claim 1, further comprising a wire loop extending from the proximal clamping jaw, the wire loop configured to effectively increase a capture area of the proximal clamping jaw.

7. The suture attachment catheter of claim 6, wherein the wire loop is configured to automatically transition from a collapsed position to an expanded position when the proximal clamping jaw is extended out of a delivery catheter in the heart.

8. The suture attachment catheter of claim 1, wherein the distal clamping jaw includes a suture routing post configured to retain a suture thereon under tension.

9. The suture attachment catheter of claim 1, wherein a perimeter of the distal clamping jaw defines a plurality of stepped teeth configured to enhance retention of the leaflet between the distal clamping jaw and the proximal clamping jaw.

10. The suture attachment catheter of claim 9, wherein the proximal clamping jaw defines a plurality of stepped teeth configured to enhance retention of the leaflet between the distal clamping jaw and the proximal clamping jaw.

11. The suture attachment catheter of claim 1, further comprising one or more fiber optic cables extending from the control handle to the proximal clamping jaw, and wherein the proximal clamping jaw includes an opening on a clamping face of the proximal clamping jaw to enable the one or more fiber optic cables to confirm capture of a valve leaflet between the proximal clamping jaw and the distal clamping jaw.

12. The suture attachment catheter of claim 1, further comprising a needle selectively slideable within the catheter body, the needle configured to be extended from the proximal clamping jaw to penetrate a valve leaflet to insert a suture through the valve leaflet when the valve leaflet is captured between the proximal clamping jaw and the distal clamping jaw.

13. The suture attachment catheter of claim 12, further comprising a needle release disposed at the control handle, and wherein the needle is prevented from extending from the proximal clamping jaw until the needle release is actuated.

14. The suture attachment catheter of claim 12, further comprising a suture configured to be retained on the distal clamping jaw for retrieval by the needle and a suture tensioning assembly disposed at the control handle, the suture tensioning assembly configured to apply tension on the suture to enable the suture to be retained on the distal clamping jaw under tension.

15. The suture attachment catheter of claim 14, further comprising a suture release pin disposed in the handle, the suture release pin configured to release the tension on the suture to enable the suture to be retrieved from the distal clamping jaw.

16. The suture attachment catheter of claim 1, wherein the suture attachment assembly is less flexible than the catheter body.

17. The suture attachment catheter of claim 1, wherein the suture attachment catheter is configured for insertion into a left atrium of the patient's heart via a vascular access to a right atrium of the heart and a transseptal access between the right atrium and the left atrium.

18. The suture attachment catheter of claim 1, wherein the rail is configured to slide in a channel of the proximal clamping jaw.

19. The suture attachment catheter of claim 18, further comprising a distal rail lock configured to prevent the rail from being slid distally beyond the proximal clamping jaw.

20. The suture attachment catheter of claim 1, further comprising a proximal rail lock configured to prevent the rail from being slid proximally to bring the distal clamping jaw closer than a predetermined minimum distance from the proximal clamping jaw.

* * * * *